United States Patent
Jagasia et al.

(10) Patent No.: US 9,586,966 B2
(45) Date of Patent: Mar. 7, 2017

(54) PIPERAZINO[1,2-A]INDOL-1-ONES AND [1,4]DIAZEPINO[1,2-A]INDOL-ONE

(71) Applicant: Hoffmann-La Roche Inc., Little Falls, NJ (US)

(72) Inventors: Ravi Jagasia, Loerrach (DE); Roland Jakob-Roetne, Inzlingen (DE); Juergen Wichmann, Steinen (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/868,059

(22) Filed: Sep. 28, 2015

(65) Prior Publication Data

US 2016/0016963 A1    Jan. 21, 2016

Related U.S. Application Data

(63) Continuation of application No. PCT/EP2014/056393, filed on Mar. 31, 2014.

(30) Foreign Application Priority Data

Apr. 2, 2013 (EP) .................... 13161949

(51) Int. Cl.
| | |
|---|---|
| *A01N 43/62* | (2006.01) |
| *A61K 31/55* | (2006.01) |
| *C07D 487/04* | (2006.01) |
| *C07D 519/00* | (2006.01) |

(52) U.S. Cl.
CPC ......... *C07D 487/04* (2013.01); *C07D 519/00* (2013.01)

(58) Field of Classification Search
None
See application file for complete search history.

(56) References Cited

U.S. PATENT DOCUMENTS

| | | |
|---|---|---|
| 2007/0135416 A1 | 6/2007 | Nettekoven et al. |
| 2009/0192147 A1 | 7/2009 | Ayral-Kaloustian et al. |

FOREIGN PATENT DOCUMENTS

| | | |
|---|---|---|
| DE | 19 28 726 | 12/1969 |
| WO | 2014/023674 | 2/2014 |

OTHER PUBLICATIONS

Markl et al. (Bioorganic & Medicinal Chemistry, 2009, 17, 4583-4594).*
Ito et al. (Cancer Science, 2003, 94, 3-8).*
Bos M. et al., "Synthesis, pharmacology and therapeutic potential of 10-methoxypyrazino [1,2-a] indoles, partial agonists at the 5HT2c receptor" European Journal of medicinal chemistry 32:253-261 (Jan. 1, 1997).
Hendi S.B et al., "Synthesis of 11-methyl-2, 3, 4, 5-tetrahydro-1H-[1,4] diaze pino [1,2-a] indoles & 1-(3-aminopropyl)-2-hydroxymethyl1-3-methyl indoles" Indian Journal of chemisty 20B:288-289 (Apr. 1, 1981).

* cited by examiner

*Primary Examiner* — Dennis Heyer
*Assistant Examiner* — Daniel M Podgorski

(57) ABSTRACT

The present invention relates to compounds of general formula I wherein $R^1$, $R^2$, $R^3$ and X are as defined

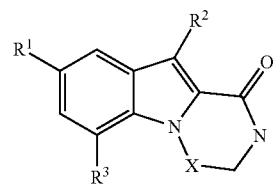

herein, or to a pharmaceutically acceptable acid addition salt or optical isomers thereof, which are useful to treat CNS disorders.

8 Claims, No Drawings

PIPERAZINO[1,2-A]INDOL-1-ONES AND [1,4]DIAZEPINO[1,2-A]INDOL-ONE

CROSS-REFERENCE TO RELATED APPLICATIONS

This application is a continuation of International Application No. PCT/EP2014/056393 having an international filing date of Mar. 31, 2014, the entire contents of which are incorporation herein by reference, and which claims benefit under 35 U.S.C. §119 to European Patent Application No. EP13161949.6 filed Apr. 2, 2013.

The present invention relates to compounds of general formula I

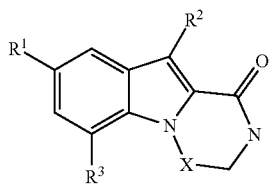

wherein
$R^1$ is halogen, lower alkyl, lower alkoxy, lower alkyl substituted by halogen, lower alkoxy substituted by halogen or cyano;
$R^2$ is hydrogen, $CF_3$ or lower alkyl;
$R^3$ is hydrogen, lower alkyl, lower alkenyl, lower alkinyl, heterocycloalkyl, lower alkyl substituted by cyano, cyano, benzyl substituted by halogen, 2-oxa-6-aza-spiro[3.3]hept-6-yl or is lower alkoxy substituted by halogen;
X is —$CH_2$— or —$CH_2$—$CH_2$—;
or to a pharmaceutically acceptable acid addition salt, to a racemic mixture or to its corresponding enantiomer and/or optical isomers thereof.

Now it has been shown that the present compounds stimulate neurogenesis from neural stem cells (NSCs). Neurogenesis occurs in the developing and adult brain. Conceptually, this process of neurogenesis can be divided into four steps: (i) proliferation of NSCs; (ii) neuronal fate determination of NSC; (iii) survival and maturation of new neurons; and (iv) functional integration of new neurons into the neuronal network.

Adult neurogenesis is a developmental process that occurs throughout live in the adult brain whereby new functional neurons are generated from adult neural stem cells. Constitutive adult neurogenesis under physiological conditions occurs mainly in two "neurogenic" brain regions, 1) the sub-granular zone (SGZ) in the dentate gyms of the hippocampus, where new dentate granule cells are generated, 2) the sub-ventricular zone (SVZ) of the lateral ventricles, where new neurons are generated and then migrate through the rostral migratory stream (RMS) to the olfactory bulb to become interneurons.

Extensive evidence suggests that hippocampal adult neurogenesis plays an important role in cognitive and emotional states albeit the precise function remains elusive. It has been argued that the relatively small number of newborn granule neurons can affect global brain function because they innervate many interneurons within the dentate gyms, each of which inhibits hundreds of mature granule cells leading to a neurogenesis-dependent feedback inhibition. In combination with a low threshold for firing the newborn neurons trigger responses to very subtle changes in context. Disturbances in this process may manifest behaviorally in deficits in pattern separation related to psychiatric diseases. For example, adult hippocampal neurogenesis correlates with cognitive and emotional capacity, e.g. physical exercise, exposure to an enriched environment and typical antidepressants concomitantly promote adult hippocampal neurogenesis and cognition and/or emotional states, while chronic stress, depression, sleep deprivation and aging decrease adult neurogenesis and associate with negative cognitive and/or emotional states (Neuron 70, May 26, 2011, pp 582-588 and pp 687-702; WO 2008/046072). Interestingly, antidepressants promote hippocampal adult neurogenesis and their effects on certain behaviors require the stimulation of neurogenesis. Neurogenesis in other adult CNS regions is generally believed to be very limited under normal physiological conditions, but could be induced after injury such as stroke, and central and peripheral brain damage.

It is therefore believed that stimulation of adult neurogenesis represents a neuro-regenerative therapeutic target for normal aging and in particular for a variety of neurodegenerative and neuropsychiatric diseases, including schizophrenia, obsessive-compulsive personality disorder, major depression, bipolar disorders, anxiety disorders, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction ("chemobrain"), Down syndrome, autism spectrum disorders, hearing loss (Neuroscience, 167 (2010) 1216-1226; Nature Medicine, Vol. 11, number 3, (2005), 271-276) tinnitus, spinocerebellar ataxia, amyotrophic lateral sclerosis, multiple sclerosis, Huntington's disease, stroke, and disturbances due to radiation therapy, chronic stress, or abuse of neuro-active drugs, such as alcohol, opiates, methamphetamine, phencyclidine and cocaine (US 2012/0022096).

Hence, chemical stimulation of adult neurogenesis offers new regenerative avenues and opportunities to develop novel drugs for treating neurological diseases and neuropsychiatric disorders.

Therefore, the object of the present invention was to identify compounds that modulate neurogenesis. It has been found that the compounds of formula I are active in this area and they may therefore be used for the treatment of schizophrenia, obsessive-compulsive personality disorder, major depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction ("chemobrain"), Down syndrome, autism spectrum disorders, hearing loss, tinnitus, spinocerebellar ataxia, amyotrophic lateral sclerosis, multiple sclerosis, Huntington's disease, stroke, and disturbances due to radiation therapy, chronic stress, or abuse of neuro-active drugs, such as alcohol, opiates, methamphetamine, phencyclidine and cocaine.

The most preferred indications for compounds of formula I are Alzheimer's disease, depression, anxiety disorders and stroke.

The present invention relates to compounds of formula I and to their pharmaceutically acceptable salts, to these compounds as pharmaceutically active substances, to the processes for their production, as well as to the use in the treatment or prevention of disorders, relating to neurogenesis, schizophrenia, obsessive-compulsive personality disorder, major depression, bipolar disorders, anxiety disorders, normal aging, epilepsy, retinal degeneration, traumatic brain injury, spinal cord injury, post-traumatic stress disorder, Parkinson's disease, dementia, Alzheimer's disease, mild cognitive impairment, chemotherapy-induced cognitive dysfunction, Down syndrome, autism spectrum disorders, hearing loss, tinnitus, spinocerebellar ataxia, amyotrophic lateral sclerosis, multiple sclerosis, Huntington's disease, stroke, radiation therapy, chronic stress, abuse of neuro-active drugs, such as alcohol, opiates, methamphetamine, phencyclidine and cocaine, and to pharmaceutical compositions containing the compounds of formula I.

The following definitions of the general terms used in the present description apply irrespective of whether the terms in question appear alone or in combination.

As used herein, the term "lower alkyl" denotes a saturated, i.e. aliphatic hydrocarbon group including a straight or branched carbon chain with 1-7 carbon atoms. Examples for "alkyl" are methyl, ethyl, n-propyl, isopropyl, n-butyl, i-butyl, 2-butyl, t-butyl and the like. Preferred alkyl groups with 1-4 carbon atoms.

As used herein, the term "lower alkenyl" denotes a hydrocarbon group including a straight or branched carbon chain with 2-7 carbon atoms, wherein at least one double bond is included, for example, —CH=CH$_2$, —CH$_2$CH=CH$_2$ and the like.

As used herein, the term "lower alkinyl" denotes a hydrocarbon group including a straight or branched carbon chain with 2-7 carbon atoms, wherein at least one triple bond is included, for example —C≡CH, —CH—C≡CH and the like.

The term "alkoxy" denotes a group —O—R' wherein R' is lower alkyl as defined above.

The term "halogen" denotes chlorine, bromine, fluorine or iodine.

The term "lower alkyl substituted by cyano" denotes an alkyl group as defined above, wherein at least one hydrogen atoms is replaced by cyano, for example CH$_2$CN, CH$_2$CH$_2$CN, CH$_2$CH$_2$CH$_2$CN and the like.

The term "heterocycloalkyl" denotes a non-aromatic ring with 5 or 6 ring atoms, containing at least one N, S or O atom, for example morpholinyl, thiomorpholinyl, 1,1-dioxo-thiomorpholinyl, piperidinyl, piperazinyl, pyrrolidinyl, tetrahydrofuranyl or tetrahydro-thiophenyl.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like One embodiment of the invention are compounds of formula

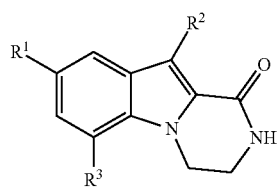

IA wherein
$R^1$ is halogen, lower alkyl, lower alkoxy, lower alkyl substituted by halogen, lower alkoxy substituted by halogen or cyano;

$R^2$ is hydrogen, CF$_3$ or lower alkyl;
$R^3$ is hydrogen, lower alkyl, lower alkenyl, lower alkinyl, heterocycloalkyl, lower alkyl substituted by cyano, cyano, benzyl substituted by halogen, 2-oxa-6-aza-spiro[3.3]hept-6-yl or is lower alkoxy substituted by halogen;
or a pharmaceutically acceptable acid addition salt, a racemic mixture or its corresponding enantiomer and/or optical isomers thereof, for example the following compounds
8-Fluoro-6-methyl-3,4-dihydro-2H-pyrazino[1,2-a]indol-1-one
8-Fluoro-6-isobutyl-10-methyl-3,4-dihydro-2H-pyrazino[1,2-a]indol-1-one
8-Fluoro-10-methyl-3,4-dihydro-2H-pyrazino[1,2-a]indol-1-one
8-Fluoro-6,10-dimethyl-3,4-dihydro-2H-pyrazino[1,2-a]indol-1-one
8-Fluoro-10-methyl-6-morpholin-4-yl-3,4-dihydro-2H-pyrazino[1,2-a]indol-1-one
8-Chloro-6,10-dimethyl-3,4-dihydro-2H-pyrazino[1,2-a]indol-1-one
6-Ethyl-8-fluoro-10-methyl-3,4-dihydro-2H-pyrazino[1,2-a]indol-1-one
6-(1,1-Dioxo-1$\lambda^6$-thiomorpholin-4-yl)-8-fluoro-10-methyl-3,4-dihydro-2H-pyrazino[1,2-a]indol-1-one
8-Chloro-6-ethyl-10-methyl-3,4-dihydro-2H-pyrazino[1,2-a]indol-1-one
6-Allyl-8-fluoro-10-methyl-3,4-dihydro-2H-pyrazino[1,2-a]indol-1-one
8-Fluoro-10-methyl-6-(3-methyl-butyl)-3,4-dihydro-2H-pyrazino[1,2-a]indol-1-one
4-(8-Fluoro-10-methyl-1-oxo-1,2,3,4-tetrahydro-pyrazino[1,2-a]indol-6-yl)-butyronitrile
8-Chloro-6-isobutyl-10-methyl-3,4-dihydro-2H-pyrazino[1,2-a]indol-1-one
8-Fluoro-6-(4-fluoro-benzyl)-10-methyl-3,4-dihydro-2H-pyrazino[1,2-a]indol-1-one
8-Fluoro-10-methyl-6-(2-oxa-6-aza-spiro[3.3]hept-6-yl)-3,4-dihydro-2H-pyrazino[1,2-a]indol-1-one
8-Chloro-6-(1,1-dioxo-1$\lambda^6$-thiomorpholin-4-yl)-10-methyl-3,4-dihydro-2H-pyrazino[1,2-a]indol-1-one
8-Chloro-10-methyl-6-morpholin-4-yl-3,4-dihydro-2H-pyrazino[1,2-a]indol-1-one
6-(1,1-Dioxo-1$\lambda^6$-thiomorpholin-4-yl)-10-methyl-1-oxo-1,2,3,4-tetrahydro-pyrazino[1,2-a]indole-8-carbonitrile
6-Ethynyl-8-fluoro-10-methyl-3,4-dihydro-2H-pyrazino[1,2-a]indol-1-one
6-Isobutyl-1-oxo-1,2,3,4-tetrahydro-pyrazino[1,2-a]indole-8-carbonitrile
8-Fluoro-6-(2-methylpropyl)-3,4-dihydro-2H-pyrazino[1,2-a]indol-1-one
8-Fluoro-10-methyl-6-(2,2,2-trifluoroethoxy)-3,4-dihydro-2H-pyrazino[1,2-a]indol-1-one
8-Chloro-6-(2-methylpropyl)-3,4-dihydro-2H-pyrazino[1,2-a]indol-1-one
8-Chloro-6-methyl-3,4-dihydro-2H-pyrazino[1,2-a]indol-1-one
8-Fluoro-10-methyl-1-oxo-3,4-dihydro-2H-pyrazino[1,2-a]indole-6-carbonitrile
10-Methyl-1-oxo-6-(trifluoromethoxy)-3,4-dihydro-2H-pyrazino[1,2-a]indole-8-carbonitrile
8-Methyl-6-(2-methylpropyl)-3,4-dihydro-2H-pyrazino[1,2-a]indol-1-one
6,8-Dimethyl-3,4-dihydro-2H-pyrazino[1,2-a]indol-1-one
8-Methoxy-6-(2-methylpropyl)-3,4-dihydro-2H-pyrazino[1,2-a]indol-1-one
6-(2-Methylpropyl)-8-(trifluoromethoxy)-3,4-dihydro-2H-pyrazino[1,2-a]indol-1-one 10-Methyl-6-morpholin-4-yl-1-oxo-3,4-dihydro-2H-pyrazino[1,2-a]indole-8-carbonitrile or 6-Morpholin-4-yl-1-oxo-3,4-dihydro-2H-pyrazino[1,2-a]indole-8-carbonitrile.

A further object of the present invention are compounds of formula

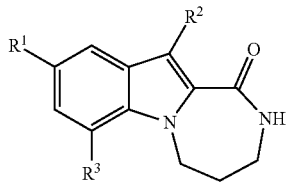

IB wherein

R¹ is halogen, lower alkyl, lower alkoxy, lower alkyl substituted by halogen, lower alkoxy substituted by halogen or cyano;

R² is hydrogen, CF₃ or lower alkyl;

R³ is hydrogen, lower alkyl, lower alkenyl, lower alkinyl, heterocycloalkyl, lower alkyl substituted by cyano, cyano, benzyl substituted by halogen, 2-oxa-6-aza-spiro[3.3]hept-6-yl or is lower alkoxy substituted by halogen;

or a pharmaceutically acceptable acid addition salt, a racemic mixture or its corresponding enantiomer and/or optical isomers thereof, for example the following compounds:

9-Fluoro-7-methyl-2,3,4,5-tetrahydro-[1,4]diazepino[1,2-a]indol-1-one

9-Fluoro-7-isobutyl-2,3,4,5-tetrahydro-[1,4]diazepino[1,2-a]indol-1-one

9-Chloro-7-(2-methylpropyl)-2,3,4,5-tetrahydro-[1,4]diazepino[1,2-a]indol-1-one

9-Chloro-7-methyl-2,3,4,5-tetrahydro-[1,4]diazepino[1,2-a]indol-1-one

9-Methyl-7-(2-methylpropyl)-2,3,4,5-tetrahydro-[1,4]diazepino[1,2-a]indol-1-one

11-Methyl-7-(2-methylpropyl)-1-oxo-2,3,4,5-tetrahydro-[1,4]diazepino[1,2-a]indole-9-carbonitrile 7,11-Dimethyl-1-oxo-2,3,4,5-tetrahydro-[1,4]diazepino[1,2-a]indole-9-carbonitrile 9-Chloro-11-methyl-7-(2-methylpropyl)-2,3,4,5-tetrahydro-[1,4]diazepino[1,2-a]indol-1-one 9-Chloro-7,11-dimethyl-2,3,4,5-tetrahydro[1,4]diazepino[1,2-a]indol-1-one 7-(2-Methylpropyl)-1-oxo-2,3,4,5-tetrahydro-[1,4]diazepino[1,2-a]indole-9-carbonitrile 7-(1,1-Dioxo-1,4-thiazinan-4-yl)-11-methyl-1-oxo-2,3,4,5-tetrahydro-[1,4]diazepino[1,2-a]indole-9-carbonitrile 7-(1,1-Dioxo-1,4-thiazinan-4-yl)-1-oxo-2,3,4,5-tetrahydro-[1,4]diazepino[1,2-a]indole-9-carbonitrile 11-Methyl-7-morpholin-4-yl-1-oxo-2,3,4,5-tetrahydro-[1,4]diazepino[1,2-a]indole-9-carbonitrile or 7-Morpholin-4-yl-1-oxo-2,3,4,5-tetrahydro-[1,4]diazepino[1,2-a]indole-9-carbonitrile.

A further object of the present invention are compounds of formula I

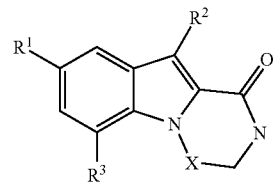

I wherein

R¹ is halogen, lower alkyl, lower alkoxy, lower alkyl substituted by halogen, lower alkoxy substituted by halogen or cyano;

R² is hydrogen, CF₃ or lower alkyl;

R³ is hydrogen, lower alkyl, lower alkenyl, lower alkinyl, heterocycloalkyl, lower alkyl substituted by cyano, cyano, benzyl substituted by halogen, 2-oxa-6-aza-spiro[3.3]hept-6-yl or is lower alkoxy substituted by halogen;

X is —CH₂— or —CH₂—CH₂—;

or a pharmaceutically acceptable acid addition salt, a racemic mixture or its corresponding enantiomer and/or optical isomers thereof for use as therapeutic active substances in the treatment of schizophrenia, obsessive-compulsive personality disorder, major depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction, Down syndrome, autism spectrum disorders, hearing loss, tinnitus, spinocerebellar ataxia, amyotrophic lateral sclerosis, multiple sclerosis, Huntington's disease, stroke, radiation therapy, chronic stress, abuse of neuro-active drugs, such as alcohol, opiates, methamphetamine, phencyclidine and cocaine.

The present compounds of formula I and their pharmaceutically acceptable salts can be prepared by methods known in the art, for example, by processes described below, which process comprises reacting a compound of formula

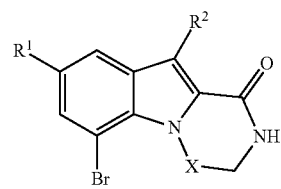

1 with a compound of formula

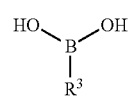

2 or in case of formation of a nitrogen carbon bond by Buchwald coupling reaction to a compound of formula

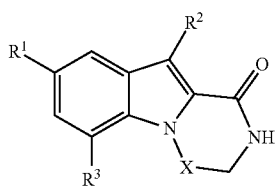

wherein the substituents are as described above, and, if desired, converting the compounds obtained into pharmaceutically acceptable acid addition salts.

The preparation of compounds of formula I of the present invention may be carried out in sequential or convergent synthetic routes. Syntheses of the compounds of the invention are shown in the following scheme 1. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

Scheme 1

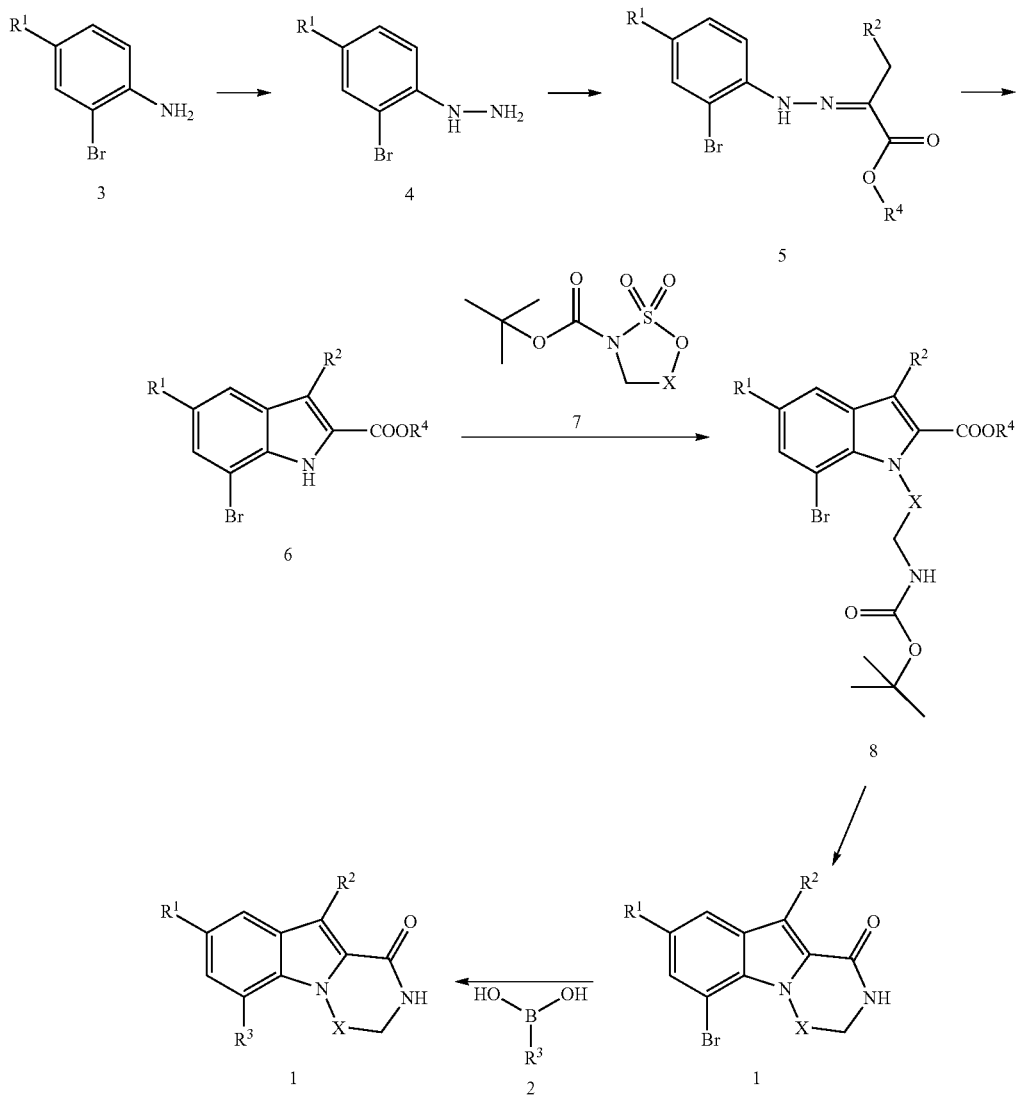

wherein the substituents are as described above, and $R^4$ is lower alkyl.

Starting from the anilines of formula 3 the corresponding hydrazines of formula 4 were prepared. These derivatives were the starting points for a classical indole synthesis yielding the indole-2-carboxylates of formula 6 via the intermediates of formula 5. N-alkylation using the commercially available reagents of formula 7 gave rise to the N-Boc protected precursors of formula 8 which were after cleavage of the protecting group converted into the building blocks of formula 1. Reaction with e.g. commercially available boronic acids yielded the final compounds of formula I.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used.

Salts of Compounds of Formula I

The compounds of formula I are basic and may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention have an activity as neurogenic agents.

The compounds were investigated in accordance with the test given hereinafter.

Neurogenesis Assay

Neural Stem Cell Proliferation Assay

Neurogenic properties of small molecules are determined based on the proliferation of human embryonic stem cell derived neural stem cells (NSCs) which were derived via a dual smad inhibition as previously described (Chambers, S. M., et al., *Highly efficient neural conversion of human ES and iPS cells by dual inhibition of SMAD signaling*, Nature biotechnology, 2009. 27(3): p. 275-80.)

Compounds respond is measured by the increase in cells based on ATP levels (Promega:CellTiterGlo®) after an incubation period of 4 days.

NSCs are thawed and expanded over 3 passages. On the 14$^{th}$ day, NSCs are seeded in Polyornithin/Laminin coated 384 well plates at a cell density of 21'000 cells/cm$^2$ in a media volume of 38 µl. 4 hours after cell seeding, compound solutions are added at a volume of 2 µl. Stock solutions of the compounds (water, 5% DMSO) are diluted to obtain a dose response (11 points, dilution factor is 2), ranging from 8 µM to 8 nM. Controls are run to consistently determine the neurogenic properties of the cells:

Negative (neutral) control is cell culture Media (final DMSO concentration: 0.25%).

Positive controls are:
1. cell culture Media+100 ng/ml FGF2 (final DMSO concentration: 0.1%)
2. cell culture Media+20 ng/ml EGF (final DMSO concentration: 0.1%)
3. cell culture Media+100 ng/ml Wnt3a (final DMSO concentration: 0.1%)

After 4 days incubation at 37° C., 5% $CO_2$, the amount of ATP per well is quantified. The ATP concentration is proportional to the cell number. ATP is quantified by using the Promega CellTiterGlo® kit. The CellTiterGlo® reagents contain a cell lysis buffer, a thermo stable luciferase (Ultra-Glo™ recombinant luciferase), magnesium and luciferin. Luciferin reacts with ATP producing oxyluciferin, AMP and light. The luminescence signal is proportional to the ATP content.

The value of negative (neutral) control is determined for each assay plate by taking the average of 16 negative control wells. The neurogenic compound response is calculated for each compound as (compound/Negative Control)*100.

The values of $EC_{150}$ from the dose response curve are determined for each test compound. The $EC_{150}$ is the compound concentration at which 150% activity of control (100%) is reached.

The preferred compounds show a $EC_{150}$ (µM) in the range of <4.0 µM as shown in the table below.

List of Examples and $EC_{150}$ Data

| Ex. | Structure | Name | $EC_{150}$ (uM) |
|---|---|---|---|
| 1 | 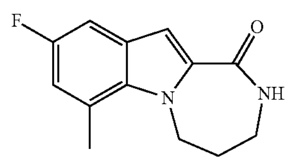 [SMILES: Cc1cc(F)cc2cc3n(c12)CCCNC3=O] | 9-Fluoro-7-methyl-2,3,4,5-tetrahydro-[1,4]diazepino[1,2-a]indol-1-one | 0.21 |

-continued

| Ex. | Structure | Name | EC$_{150}$ (uM) |
|---|---|---|---|
| 2 | 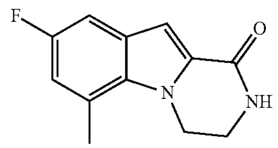 [SMILES: Cc1cc(F)cc2cc3n(c12)CCNC3=O] | 8-Fluoro-6-methyl-3,4-dihydro-2H-pyrazino[1,2-a]indol-1-one | 0.17 |
| 3 | 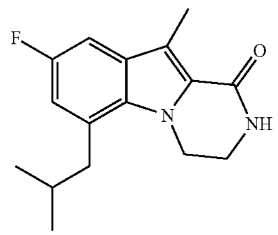 [SMILES: Cc1c2n(c3c(CC(C)C)cc(F)cc13)CCNC2=O] | 8-Fluoro-6-isobutyl-10-methyl-3,4-dihydro-2H-pyrazino[1]indol-1-one | 0.009 |
| 4 | 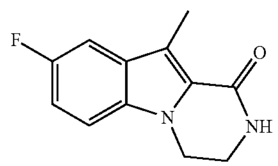 [SMILES: Cc1c2n(c3ccc(F)cc13)CCNC2=O] | 8-Fluoro-10-methyl-3,4-dihydro-2H-pyrazino[1,2-a]indol-1-one | 0.31 |
| 5 | 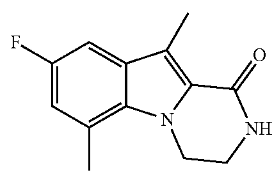 [SMILES: Cc1c2n(c3c(C)cc(F)cc13)CCNC2=O] | 8-Fluoro-6,10-dimethyl-3,4-dihydro-2H-pyrazino[1,2-a]indol-1-one | 0.074 |
| 6 | 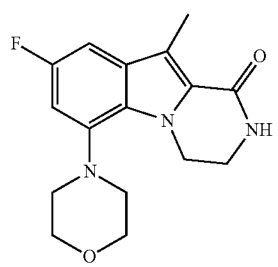 [SMILES: Cc1c2n(c3c(N4CCOCC4)cc(F)cc13)CCNC2=O] | 8-Fluoro-10-methyl-6-morpholin-4-yl-3,4-dihydro-2H-pyrazino[1,2-a]indol-1-one | 0.21 |
| 7 | 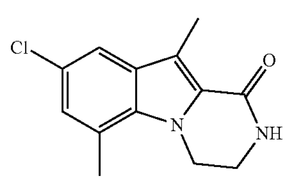 [SMILES: Cc1c2n(c3c(C)cc(Cl)cc13)CCNC2=O] | 8-Chloro-6,10-dimethyl-3,4-dihydro-2H-pyrazino[1,2-a]indol-1-one | 0.11 |
| 8 | 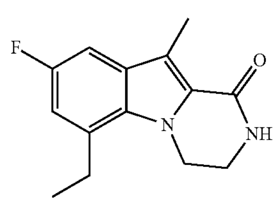 [SMILES: CCc1cc(F)cc2c(C)c3n(c12)CCNC3=O] | 6-Ethyl-8-fluoro-10-methyl-3,4-dihydro-2H-pyrazino[1,2-a]indol-1-one | 0.019 |

-continued

| Ex. | Structure | Name | EC₁₅₀ (uM) |
|---|---|---|---|
| 9 | 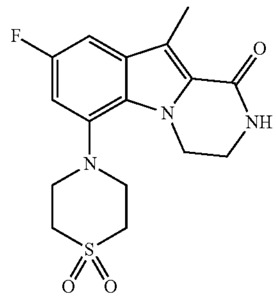 [SMILES: Cc1c2n(c3c(N4CCS(=O)(=O)CC4)cc(F)cc13)CCNC2=O] | 6-(1,1-Dioxo-1λ⁶-thiomorpholin-4-yl)-8-fluoro-10-methyl-3,4-dihydro-2H-pyrazino[1,2-a]indol-1-one | 0.015 |
| 10 | 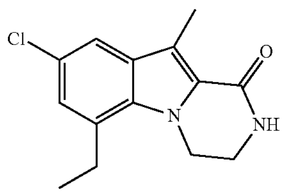 [SMILES: CCc1cc(Cl)cc2c(C)c3n(c12)CCNC3=O] | 8-Chloro-6-ethyl-10-methyl-3,4-dihydro-2H-pyrazino[1,2-a]indol-1-one | 0.34 |
| 11 | 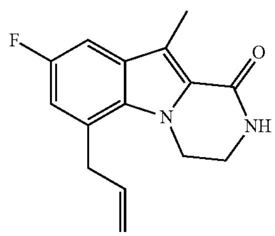 [SMILES: C=CCc1cc(F)cc2c(C)c3n(c12)CCNC3=O] | 6-Allyl-8-fluoro-10-methyl-3,4-dihydro-2H-pyrazino[1,2-a]indol-1-one | 0.14 |
| 12 | 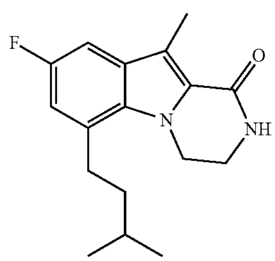 [SMILES: Cc1c2n(c3c(CCC(C)C)cc(F)cc13)CCNC2=O] | 8-Fluoro-10-methyl-6-(3-methyl-butyl)-3,4-dihydro-2H-pyrazino[1,2-a]indol-1-one | 0.07 |
| 13 | 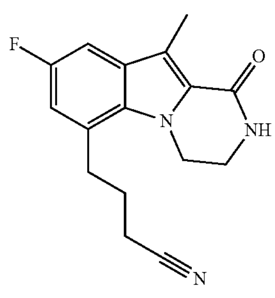 [SMILES: Cc1c2n(c3c(CCCC#N)cc(F)cc13)CCNC2=O] | 4-(8-Fluoro-10-methyl-1-oxo-1,2,3,4-tetrahydro-pyrazino[1,2-a]indol-6-yl)-butyronitrile | 0.31 |
| 14 | 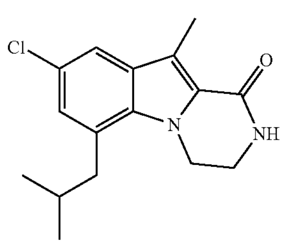 [SMILES: Cc1c2n(c3c(CC(C)C)cc(Cl)cc13)CCNC2=O] | 8-Chloro-6-isobutyl-10-methyl-3,4-dihydro-2H-pyrazino[1]indol-1-one | 0.19 |

| Ex. | Structure | Name | EC$_{150}$ (uM) |
|---|---|---|---|
| 15 | 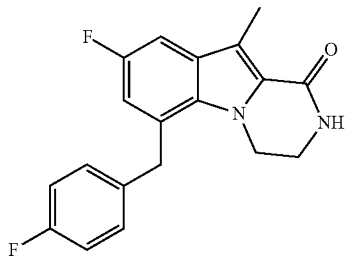 [SMILES: Cc1c2n(c3c(Cc4ccc(F)cc4)cc(F)cc13)CCNC2=O] | 8-Fluoro-6-(4-fluoro-benzyl)-10-methyl-3,4-dihydro-2H-pyrazino[1,2-a]indol-1-one | 0.16 |
| 16 | 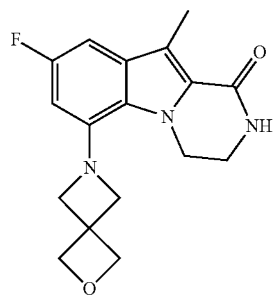 [SMILES: Cc1c2n(c3c(N4CC5(COC5)C4)cc(F)cc13)CCNC2=O] | 8-Fluoro-10-methyl-6-(2-oxa-6-aza-spiro[3.3]hept-6-yl)-3,4-dihydro-2H-pyrazino[1,2-a]indol-1-one | 0.23 |
| 17 | 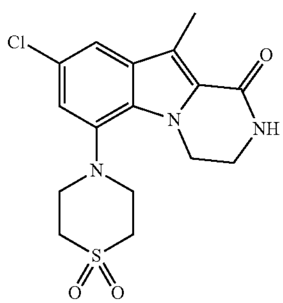 [SMILES: Cc1c2n(c3c(N4CCS(=O)(=O)CC4)cc(Cl)cc13)CCNC2=O] | 8-Chloro-6-(1,1-dioxo-1λ$^6$-thiomorpholin-4-yl)-10-methyl-3,4-dihydro-2H-pyrazino[1,2-a]indol-1-one | 0.011 |
| 18 | 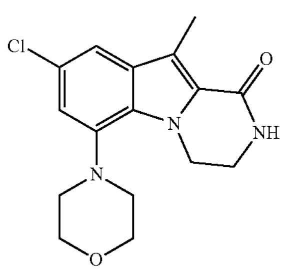 [SMILES: Cc1c2n(c3c(N4CCOCC4)cc(Cl)cc13)CCNC2=O] | 8-Chloro-10-methyl-6-morpholin-4-yl-3,4-dihydro-2H-pyrazino[1,2-a]indol-1-one | 0.039 |
| 19 | 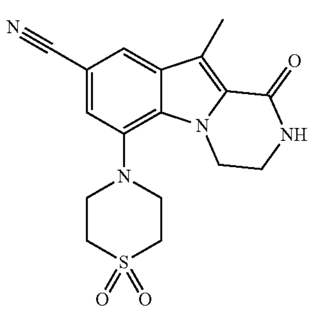 [SMILES: Cc1c2n(c3c(N4CCS(=O)(=O)CC4)cc(C#N)cc13)CCNC2=O] | 6-(1,1-Dioxo-1λ$^6$-thiomorpholin-4-yl)-10-methyl-1-oxo-1,2,3,4-tetrahydro-pyrazino[1,2-a]indole-8-carbonitrile | 0.008 |

-continued

| Ex. | Structure | Name | EC$_{150}$ (uM) |
|---|---|---|---|
| 20 | 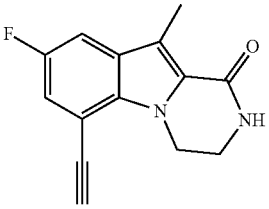 [SMILES: C#Cc1cc(F)cc2c(C)c3n(c12)CCNC3=O] | 6-Ethynyl-8-fluoro-10-methyl-3,4-dihydro-2H-pyrazino[1,2-a]indol-1-one | 0.04 |
| 21 | 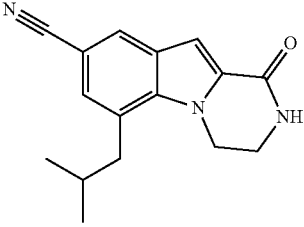 [SMILES: CC(C)Cc1cc(C#N)cc2cc3n(c12)CCNC3=O] | 6-Isobutyl-1-oxo-1,2,3,4-tetrahydro-pyrazino[1,2-a]indole-8-carbonitrile | 0.14 |
| 22 | 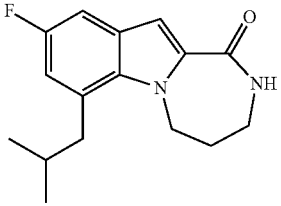 [SMILES: CC(C)Cc1cc(F)cc2cc3n(c12)CCCNC3=O] | 9-Fluoro-7-isobutyl-2,3,4,5-tetrahydro-[1,4]diazepino[1,2-a]indol-1-one | 0.11 |
| 23 | 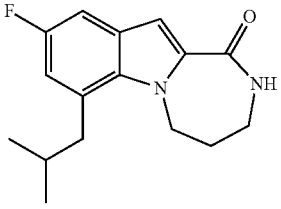 [SMILES: CC(C)Cc1cc(F)cc2cc3n(c12)CCCNC3=O] | 8-Fluoro-6-(2-methylpropyl)-3,4-dihydro-2H-pyrazino[1,2-a]indol-1-one | 0.02 |
| 24 | 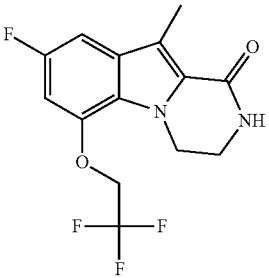 [SMILES: Cc1c2n(c3c(OCC(F)(F)F)cc(F)cc13)CCNC2=O] | 8-Fluoro-10-methyl-6-(2,2,2-trifluoroethoxy)-3,4-dihydro-2H-pyrazino[1,2-a]indol-1-one | 0.17 |
| 25 | 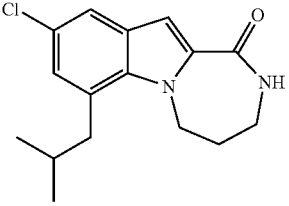 [SMILES: CC(C)Cc1cc(Cl)cc2cc3n(c12)CCCNC3=O] | 9-Chloro-7-(2-methylpropyl)-2,3,4,5-tetrahydro-[1,4]diazepino[1,2-a]indol-1-one | 1.15 |

| Ex. | Structure | Name | EC$_{150}$ (uM) |
|---|---|---|---|
| 26 | 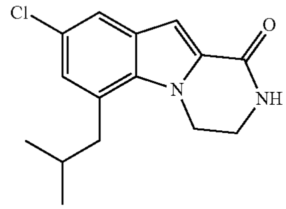 [SMILES: CC(C)Cc1cc(Cl)cc2cc3n(c12)CCNC3=O] | 8-Chloro-6-(2-methylpropyl)-3,4-dihydro-2H-pyrazino[1,2-a]indol-1-one | 0.16 |
| 27 | 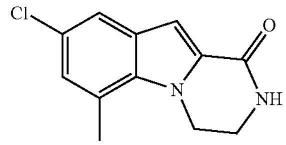 [SMILES: Cc1cc(Cl)cc2cc3n(c12)CCNC3=O] | 8-Chloro-6-methyl-3,4-dihydro-2H-pyrazino[1,2-a]indol-1-one | 5.1 |
| 28 | 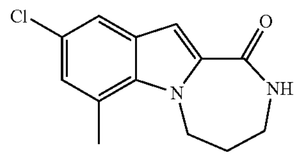 [SMILES: Cc1cc(Cl)cc2cc3n(c12)CCCNC3=O] | 9-Chloro-7-methyl-2,3,4,5-tetrahydro-[1,4]diazepino[1,2-a]indol-1-one | 4.1 |
| 29 | 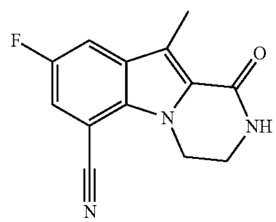 [SMILES: Cc1c2n(c3c(C#N)cc(F)cc13)CCNC2=O] | 8-Fluoro-10-methyl-1-oxo-3,4-dihydro-2H-pyrazino[1,2-a]indole-6-carbonitrile | 0.5 |
| 30 | 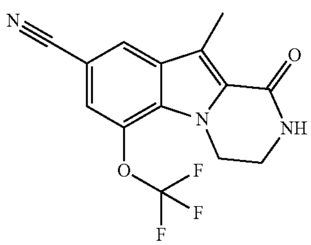 [SMILES: Cc1c2n(c3c(OC(F)(F)F)cc(C#N)cc13)CCNC2=O] | 10-Methyl-1-oxo-6-(trifluoromethoxy)-3,4-dihydro-2H-pyrazino[1,2-a]indole-8-carbonitrile | 0.11 |
| 31 | 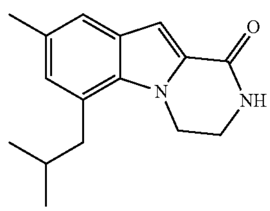 [SMILES: Cc1cc(CC(C)C)c2c(c1)cc1n2CCNC1=O] | 8-Methyl-6-(2-methylpropyl)-3,4-dihydro-2H-pyrazino[1,2-a]indol-1-one | 1.16 |
| 32 | 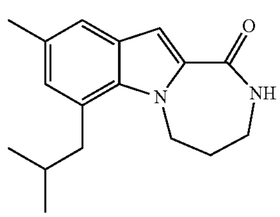 [SMILES: Cc1cc(CC(C)C)c2c(c1)cc1n2CCCNC1=O] | 9-Methyl-7-(2-methylpropyl)-2,3,4,5-tetrahydro-[1,4]diazepino[1,2-a]indol-1-one | 2.6 |
| 33 | 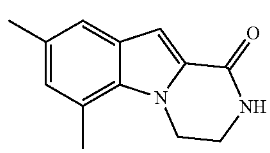 [SMILES: Cc1cc(C)c2c(c1)cc1n2CCNC1=O] | 6,8-Dimethyl-3,4-dihydro-2H-pyrazino[1,2-a]indol-1-one | 4.9 |

-continued

| Ex. | Structure | Name | EC$_{150}$ (uM) |
|---|---|---|---|
| 34 | 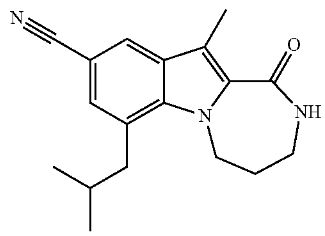 [SMILES: Cc1c2n(c3c(CC(C)C)cc(C#N)cc13)CCCNC2=O] | 11-Methyl-7-(2-methylpropyl)-1-oxo-2,3,4,5-tetrahydro-[1,4]diazepino[1,2-a]indole-9-carbonitrile | 0.13 |
| 35 | 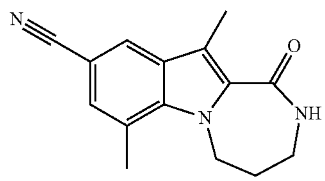 [SMILES: Cc1c2n(c3c(C)cc(C#N)cc13)CCCNC2=O] | 7,11-Dimethyl-1-oxo-2,3,4,5-tetrahydro-[1,4]diazepino[1,2-a]indole-9-carbonitrile | 3.19 |
| 36 | 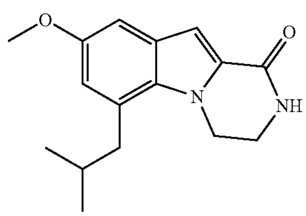 [SMILES: COc1cc(CC(C)C)c2c(c1)cc1n2CCNC1=O] | 8-Methoxy-6-(2-methylpropyl)-3,4-dihydro-2H-pyrazino[1,2-a]indol-1-one | 4.1 |
| 37 | 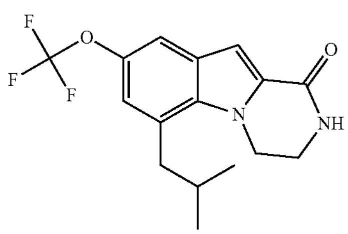 [SMILES: CC(C)Cc1cc(OC(F)(F)F)cc2cc3n(c12)CCNC3=O] | 6-(2-Methylpropyl)-8-(trifluoromethoxy)-3,4-dihydro-2H-pyrazino[1,2-a]indol-1-one | 0.89 |
| 38 | 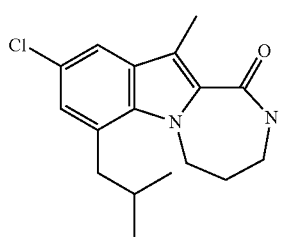 [SMILES: Cc1c2n(c3c(CC(C)C)cc(Cl)cc13)CCCNC2=O] | 9-Chloro-11-methyl-7-(2-methylpropyl)-2,3,4,5-tetrahydro-[1,4]diazepino[1,2-a]indol-1-one | 0.37 |
| 39 | 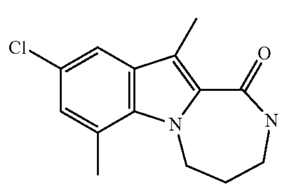 [SMILES: Cc1c2n(c3c(C)cc(Cl)cc13)CCCNC2=O] | 9-Chloro-7,11-dimethyl-2,3,4,5-tetrahydro-[1,4]diazepino[1,2-a]indol-1-one | 0.36 |
| 40 | 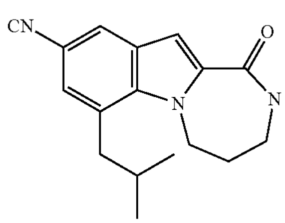 | 7-(2-Methylpropyl)-1-oxo-2,3,4,5-tetrahydro-[1,4]diazepino[1,2-a]indole-9-carbonitrile | 0.55 |

-continued

| Ex. | Structure | Name | EC$_{150}$ (uM) |
|---|---|---|---|
| 41 | 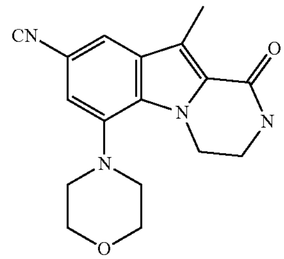 | 10-Methyl-6-morpholin-4-yl-1-oxo-3,4-dihydro-2H-pyrazino[1,2-a]indole-8-carbonitrile | 0.092 |
| 42 | 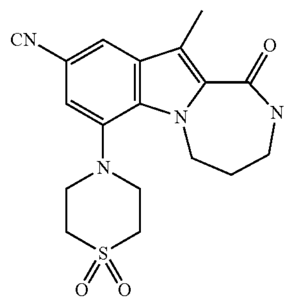 | 7-(1,1-Dioxo-1,4-thiazinan-4-yl)-11-methyl-1-oxo-2,3,4,5-tetrahydro-[1,4]diazepino[1,2-a]indole-9-carbonitrile | 0.077 |
| 43 | 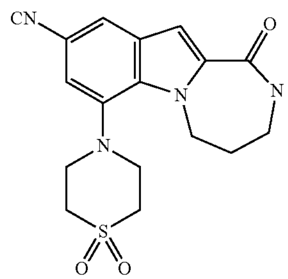 | 7-(1,1-Dioxo-1,4-thiazinan-4-yl)-1-oxo-2,3,4,5-tetrahydro-[1,4]diazepino[1,2-a]indole-9-carbonitrile | 0.98 |
| 44 | 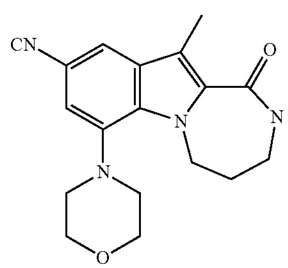 | 11-Methyl-7-morpholin-4-yl-1-oxo-2,3,4,5-tetrahydro-[1,4]diazepino[1,2-a]indole-9-carbonitrile | 0.046 |
| 45 | 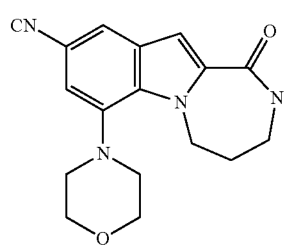 | 7-Morpholin-4-yl-1-oxo-2,3,4,5-tetrahydro-[1,4]diazepino[1,2-a]indole-9-carbonitrile | 0.24 |
| 46 | 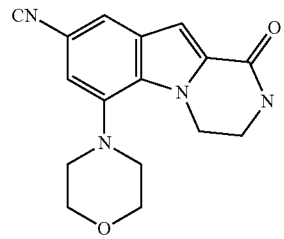 | 6-Morpholin-4-yl-1-oxo-3,4-dihydro-2H-pyrazino[1,2-a]indole-8-carbonitrile | 0.04 |

The compounds of formula (I) and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula (I) and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula (I) or pharmaceutically acceptable salts thereof and a therapeutically inert excipient are also an object of the present invention, as is a process for the production of such medicaments which comprises bringing one or more compounds of formula (I) or pharmaceutically acceptable salts thereof and, if desired, one or more other therapeutically valuable substances into a galenical dosage form together with one or more therapeutically inert carriers.

As further mentioned earlier, the use of the compounds of formula (I) for the preparation of medicaments useful in the prevention and/or the treatment of the above recited diseases is also an object of the present invention.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

Pharmaceutical Compositions Comprising Compounds of the Invention

| | Tablet Formulation (Wet Granulation) | | | | |
|---|---|---|---|---|---|
| | | | mg/tablet | | |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| | Capsule Formulation | | | | |
|---|---|---|---|---|---|
| | | | mg/capsule | | |
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

Experimental Part

Intermediates

Intermediate 1

6-Bromo-8-fluoro-3,4-dihydro-2H-pyrazino[1,2-a]indol-1-one

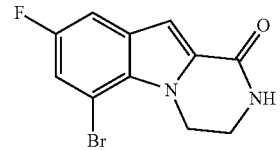 [SMILES: O=C1NCCn2c1cc1cc(F)cc(Br)c12]

Step A

To a stirred mixture of sodium hydride [disp. 55-65%] (175 mg, 4.37 mmol) in DMF (5.6 ml) was added drop wise at room temperature under argon atmosphere a solution of commercially available ethyl 7-bromo-5-fluoro-1H-indole-2-carboxylate [CAS No. 396076-60-1] (1.04 g, 3.64 mmol) in DMF (2.8 ml). Afterwards the mixture was allowed to stir for 5 min at room temperature, then commercially available 2,2-dioxo-[1,2,3]oxathiazolidine-3-carboxylic acid tert-butyl ester [CAS No. 459817-82-4] (975 mg, 4.37 mmol) was added and the solution was allowed to stir at room temperature for 15 h. The solution was cooled in an ice bath, and citric acid (10%, 62 ml) was added drop wise. The mixture was allowed to stir at room temperature for 1 h, and was afterwards extracted with ethyl acetate (2×70 ml). The combined organic layers were washed with brine (80 ml), dried (MgSO$_4$) and evaporated. The crude material (2.04 g) was purified by flash chromatography on silica gel (heptan/ethyl acetate 0-80%) to yield 7-bromo-1-(2-tert-butoxycarbonylamino-ethyl)-5-fluoro-1H-indole-2-carboxylic acid ethyl ester as a light yellow oil (1.37 g, 88%), MS (ISN) m/z=431.2 [(M+H)$^+$].

Step B

To a stirred solution of ethyl 7-bromo-1-(2-(tert-butoxycarbonylamino)ethyl)-5-fluoro-1H-indole-2-carboxylate (step A) (1.43 g, 3.33 mmol) in dichloromethane (15.2 ml) was added drop wise at 0° C. trifluoroacetic acid (4.79 g, 3.23 ml, 42.0 mmol). Afterwards the solution was allowed to stir for 15 min at 0° C., and for 30 min at room temperature. The reaction mixture was evaporated and the remaining material was solved in methanol (15.2 ml). Potassium carbonate (1.83 g, 13.3 mmol) was added and the mixture was allowed to stir at room temperature for 17 h. The mixture was evaporated, water (50 ml) was added and the mixture was extracted with dichloromethane (2×40 ml). The combined organic layers were washed with brine (50 ml), dried (MgSO$_4$) and evaporated. The crude product (0.86 g) was purified by trituration with dichloromethane (3 ml) and heptane (15 ml) to yield the title compound as an off-white solid (0.85 g, 90%), MS (ISN) m/z=283.2 [(M+H)$^+$], mp 253.5° C.

Intermediate 2

7-Bromo-9-fluoro-2,3,4,5-tetrahydro-[1,4]diazepino[1,2-a]indol-1-one

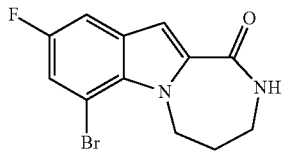 [SMILES: O=C1NCCCn2c1cc1cc(F)cc(Br)c12]

Step A

7-Bromo-1-(3-tert-butoxycarbonylamino-propyl)-5-fluoro-1H-indole-2-carboxylic acid ethyl ester, yellow oil (0.29 g, 74%), MS (ISP) m/z=443.2 [(M+H)$^+$], was prepared in accordance with the general method of intermediate 1, step A, from commercially available ethyl 7-bromo-5-fluoro-1H-indole-2-carboxylate [CAS No. 396076-60-1] (0.25 g, 0.88 mmol) and commercially available 2,2-dioxo-2λ'-[1,2,3]oxathiazinane-3-carboxylic acid tert-butyl ester [CAS No. 521267-18-5] (0.25 g, 1.06 mmol).

Step B

The title compound, off-white solid (0.14 g, 71%), MS (ISP) m/z=297.2 [(M+H)$^+$], mp 249° C., was prepared in accordance with the general method of intermediate 1, step B, from 7-bromo-1-(3-tert-butoxycarbonylamino-propyl)-5-fluoro-1H-indole-2-carboxylic acid ethyl ester (step A) (0.29 g, 0.66 mmol).

Intermediate 3

(RS)-7-Bromo-9-fluoro-5-methyl-2,3,4,5-tetrahydro-[1,4]diazepino[1,2-a]indol-1-one

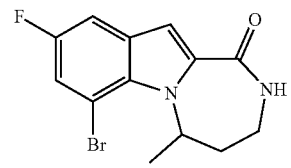 [SMILES: CC1CCNC(=O)c2cc3cc(F)cc(Br)c3n21]

Step A

7-Bromo-1-(3-tert-butoxycarbonylamino-1-methyl-propyl)-5-fluoro-1H-indole-2-carboxylic acid ethyl ester, yellow oil (0.38 g, 19%), MS (ISP) m/z=457.2 [(M+H)$^+$], was prepared in accordance with the general method of intermediate 1, step A, from commercially available ethyl 7-bromo-5-fluoro-1H-indole-2-carboxylate [CAS No. 396076-60-1] (1.25 g, 4.38 mmol) and 2,2-dioxo-6-methyl-2λ'-[1,2,3]oxathiazinane-3-carboxylic acid tert-butyl ester [CAS No. 1311368-91-8] (1.32 g, 5.25 mmol).

Step B

The title compound, light yellow solid (0.2 g, 77%), MS (ISP) m/z=313.1 [(M+H)$^+$], mp 152.5° C., was prepared in accordance with the general method of intermediate 1, step B, from 7-bromo-1-(3-tert-butoxycarbonylamino-1-methyl-propyl)-5-fluoro-1H-indole-2-carboxylic acid ethyl ester (step A) (0.38 g, 0.83 mmol).

Intermediate 4

6-Bromo-8,9-difluoro-3,4-dihydro-2H-pyrazino[1,2-a]indol-1-one

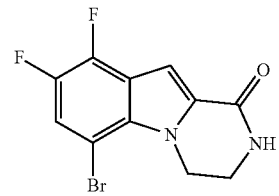 [SMILES: O=C1NCCn2c1cc1c(F)c(F)cc(Br)c12]

Step A

A stirred mixture of commercially available 2-bromo-4,5-difluoro-aniline (5 g, 24.0 mmol) and hydrochloric acid (25%, 22.9 ml) was cooled to 0° C., a solution of sodium nitrite (1.91 g, 27.6 mmol) in water (15 ml) was added drop wise over 15 min (the temperature should not rise above 10° C.). After the mixture was allowed to stir at 0° C. for 1 h, a solution of tin (II) chloride (20.5 g, 108 mmol) in hydrochloric acid (25%, 34.2 ml) was added drop wise at 0° C. (the temperature not rise above 10° C.). After the reaction mixture was allowed to stir for 1 hr at 0° C., the formed precipitate was collected by filtration and washed with water and heptane. Water (46 ml) and sodium hydroxide solution (37%, 25 ml) was added to the crude product, and the mixture was extracted with dichloromethane (3×70 ml). The combined organic layers were washed with brine (100 ml), dried (MgSO$_4$) and evaporated.

The crude product (4.75 g) was further purified by trituration with heptane (25 ml) to yield (2-bromo-4,5-difluorophenyl)-hydrazine as a light brown solid (4.29 g, 80%), MS (EI) m/z=222.0 [(M)⁺], mp 98° C.

Step B

A stirred solution of (2-bromo-4,5-difluoro-phenyl)-hydrazine (step A) (4.29 g, 19.2 mmol) in ethanol (13.8 ml) was cooled to 0° C. and a solution of ethyl pyruvate (2.39 g, 2.3 ml, 20.0 mmol) in ethanol (4 ml) was added drop wise at 0° C. for 15 min. After the mixture was allowed to stir at room temperature for 22 h it was evaporated to give crude (Z)-ethyl 2-[2-(2-bromo-4,5-difluoro-phenyl)-hydrazono]-propanoate (6.18 g, 100%) as light brown solid, MS (ISP) m/z=323.0 [(M+H)⁺], mp 78° C., which was used without further purification.

Step C

A mixture of (Z)-ethyl 2-[2-(2-bromo-4,5-difluoro-phenyl)-hydrazono]-propanoate (step B) (6.18 g, 19.2 mmol) and commercially available Eaton's reagent (7.7 wt % phosphorus pentoxide solution in methanesulfonic acid) (46.6 ml) was allowed to stir for 2 h at 50° C. Afterwards the reaction mixture was carefully poured into saturated sodium carbonate solution (200 ml), and sodium bicarbonate was added to reach pH 8-9. The reaction mixture was extracted with dichloromethane (3×70 ml). The combined organic layers were washed with brine (100 ml), dried (MgSO₄) and evaporated. The crude product (5.76 g) was further purified by column chromatography on silica gel (heptane/ethyl acetate 4:1) and trituration with diethyl ether and heptane to yield ethyl 7-bromo-4,5-difluoro-1H-indole-2-carboxylate as a light brown solid, MS (ISP) m/z=304.0 [(M+H)⁺], mp 214° C.

Step D

7-Bromo-1-(2-tert-butoxycarbonylamino-ethyl)-4,5-difluoro-1H-indole-2-carboxylic acid ethyl ester, light yellow solid (1.6 g, 94%), MS (ISP) m/z=449.0 [(M+H)⁺], mp 127° C., was prepared in accordance with the general method of intermediate 1, step A, from ethyl 7-bromo-4,5-difluoro-1H-indole-2-carboxylate (step C) (1.16 g, 3.8 mmol) and commercially available 2,2-dioxo-[1,2,3]oxathiazolidine-3-carboxylic acid tert-butyl ester [CAS No. 459817-82-4] (1.02 g, 4.56 mmol).

Step E

The title compound, white solid (1.05 g, 98%), MS (ISP) m/z=303.1 [(M+H)⁺], mp 242.5° C., was prepared in accordance with the general method of intermediate 1, step B, from 7-bromo-1-(2-tert-butoxycarbonylamino-ethyl)-4,5-difluoro-1H-indole-2-carboxylic acid ethyl ester (step D) (1.59 g, 3.55 mmol).

Intermediate 5

7-Bromo-9-chloro-2,3,4,5-tetrahydro-[1,4]diazepino[1,2-a]indol-1-one

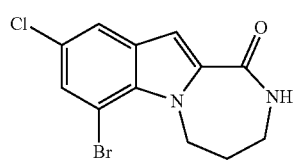 [SMILES: O=C1NCCCn2c1cc1cc(Cl)cc(Br)c12]

Step A

7-Bromo-1-(3-tert-butoxycarbonylamino-propyl)-5-chloro-1H-indole-2-carboxylic acid ethyl ester, light yellow solid (1.48 g, 85%), MS (ISP) m/z=461.2 [(M+H)⁺], mp 115.5° C., was prepared in accordance with the general method of intermediate 1, step A, from commercially available ethyl 7-bromo-5-chloro-1H-indole-2-carboxylate [CAS No. 1352896-41-3] (1.15 g, 3.8 mmol) and commercially available 2,2-dioxo-2λ'-[1,2,3]oxathiazinane-3-carboxylic acid tert-butyl ester [CAS No. 521267-18-5] (1.08 g, 4.56 mmol).

Step B

The title compound, light yellow solid (0.88 g, 88%), MS (ISP) m/z=314.9 [(M+H)⁺], mp 219° C., was prepared in accordance with the general method of intermediate 1, step B, from 7-bromo-1-(3-tert-butoxycarbonylamino-propyl)-5-chloro-1H-indole-2-carboxylic acid ethyl ester (step A) (1.47 g, 3.2 mmol).

Intermediate 6

6-Bromo-8-chloro-3,4-dihydro-2H-pyrazino[1,2-a]indol-1-one

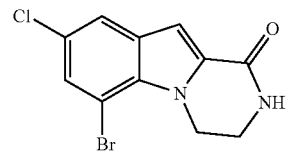 [SMILES: O=C1NCCn2c1cc1cc(Cl)cc(Br)c12]

Step A

7-Bromo-1-(2-tert-butoxycarbonylamino-ethyl)-5-chloro-1H-indole-2-carboxylic acid ethyl ester, yellow oil (1.36 g, 80%), MS (ISP) m/z=447.0 [(M+H)⁺], was prepared in accordance with the general method of intermediate 1, step A, from commercially available ethyl 7-bromo-5-chloro-1H-indole-2-carboxylate [CAS No. 1352896-41-3] (1.15 g, 3.8 mmol) and commercially available 2,2-dioxo-[1,2,3]oxathiazolidine-3-carboxylic acid tert-butyl ester [CAS No. 459817-82-4] (1.02 g, 4.56 mmol).

Step B

The title compound, white solid (0.74 g, 82%), MS (ISP) m/z=301.0 [(M+H)⁺], mp 247° C., was prepared in accordance with the general method of intermediate 1, step B, from 7-bromo-1-(2-tert-butoxycarbonylamino-ethyl)-5-chloro-1H-indole-2-carboxylic acid ethyl ester (step A) (1.35 g, 3.03 mmol).

Intermediate 7

6-Bromo-8-methyl-3,4-dihydro-2H-pyrazino[1,2-a]indol-1-one

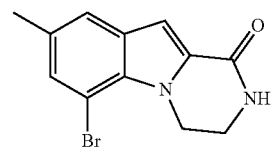 [SMILES: Cc1cc(Br)c2c(c1)cc1n2CCNC1=O]

Step A

7-Bromo-1-(2-tert-butoxycarbonylamino-ethyl)-5-methyl-1H-indole-2-carboxylic acid ethyl ester, orange solid (0.41 g, 85%), MS (ISP) m/z=325.4 [(M+H)⁺], mp 92.5° C., was prepared in accordance with the general method of intermediate 1, step A, from commercially available ethyl 7-bromo-5-methyl-1H-indole-2-carboxylate [CAS No.

15936-72-8] (0.32 g, 1.12 mmol) and commercially available 2,2-dioxo-[1,2,3]oxathiazolidine-3-carboxylic acid tert-butyl ester [CAS No. 459817-82-4] (0.3 g, 1.35 mmol).

Step B

The title compound, white solid (0.23 g, 86%), MS (ISP) m/z=279.3 [(M+H)⁺], mp 243° C., was prepared in accordance with the general method of intermediate 1, step B, from 7-bromo-1-(2-tert-butoxycarbonylamino-ethyl)-5-methyl-1H-indole-2-carboxylic acid ethyl ester (step A) (0.4 g, 0.95 mmol).

Intermediate 8

7-Bromo-9-methyl-2,3,4,5-tetrahydro-[1,4]diazepino[1,2-a]indol-1-one

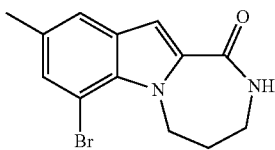 [SMILES: Cc1cc(Br)c2c(c1)cc1n2CCCNC1=O]

Step A

7-Bromo-1-(3-tert-butoxycarbonylamino-propyl)-5-methyl-1H-indole-2-carboxylic acid ethyl ester, off-white solid (0.38 g, 78%), MS (ISP) m/z=339.4 [(M+H)⁺], mp 107.5° C., was prepared in accordance with the general method of intermediate 1, step A, from commercially available ethyl 7-bromo-5-methyl-1H-indole-2-carboxylate [CAS No. 1352896-41-3] (0.32 g, 1.12 mmol) and commercially available 2,2-dioxo-2λ'-[1,2,3]oxathiazinane-3-carboxylic acid tert-butyl ester [CAS No. 521267-18-5] (0.32 g, 1.35 mmol).

Step B

The title compound, white solid (0.22 g, 86%), MS (ISP) m/z=293.4 [(M+H)⁺], mp 232° C., was prepared in accordance with the general method of intermediate 1, step B, from 7-bromo-1-(3-tert-butoxycarbonylamino-propyl)-5-methyl-1H-indole-2-carboxylic acid ethyl ester (step A) (0.38 g, 0.86 mmol).

Intermediate 9

6-Bromo-8-chloro-10-methyl-3,4-dihydro-2H-pyrazino[1,2-a]indol-1-one

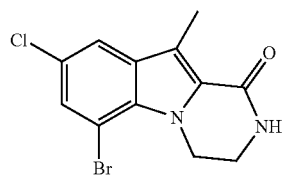 [SMILES: Cc1c2n(c3c(Br)cc(Cl)cc13)CCNC2=O]

Step A (2-Bromo-4-chloro-phenyl)-hydrazine, off-white solid (1.98 g, 60%), MS (ISP) m/z=223.3 [(M+H)⁺], mp 102° C., was prepared in accordance with the general method of intermediate 4, step A, from commercially available 2-bromo-4-chloro-aniline (3.1 g, 15.0 mmol).

Step B

A stirred solution of (2-bromo-4-chloro-phenyl)-hydrazine (step A) (1.98 g, 8.94 mmol) in ethanol (6.5 ml) was cooled to 0° C. and a solution of commercially available methyl 2-ketobutyrate (1.08 g, 1.04 ml, 9.3 mmol) in ethanol (2 ml) was added drop wise at 0° C. for 15 min. After the mixture was allowed to stir at room temperature for 3 h it was evaporated. The crude material (3.01 g) was purified by flash chromatography on silica gel (heptane/ethyl acetate 0-20%) to yield (Z)-2-[(2-bromo-4-chloro-phenyl)-hydrazono]-butyric acid methyl ester (2.67 g, 94%) as a light yellow solid, MS (ISP) m/z=321.3 [(M+H)⁺], mp 67° C.

Step C

To a stirred solution of (Z)-2-[(2-bromo-4-chloro-phenyl)-hydrazono]-butyric acid methyl ester (step B) (2.67 g, 8.35 mmol) in acetic acid (30 ml) was added at room temperature zinc chloride (6.26 g, 46.0 mmol) and the mixture was allowed to stir for 1 h under reflux conditions. Afterwards the reaction mixture was poured into ice/water (50 ml) and extracted with ethyl acetate (2×50 ml). The combined organic layers were washed with brine (50 ml), dried (MgSO₄) and evaporated. The crude product (2.5 g) was further purified by flash chromatography on silica gel (heptane/ethyl acetate 0-20%) and trituration with diethyl ether (5 ml) and heptane (15 ml) to yield methyl 7-bromo-5-chloro-3-methyl-1H-indole-2-carboxylate as an off-white solid (2.02 g, 80%), MS (ISN) m/z=302.3 [(M−H)⁻], mp 163.5° C.

Step D

7-Bromo-1-(2-tert-butoxycarbonylamino-ethyl)-5-chloro-3-methyl-1H-indole-2-carboxylic acid ethyl ester, light yellow oil (1.45 g, 97%), MS (ISP) m/z=447.3 [(M+H)⁺], was prepared in accordance with the general method of intermediate 1, step A, from methyl 7-bromo-5-chloro-3-methyl-1H-indole-2-carboxylate (step C) (1.01 g, 3.34 mmol) and commercially available 2,2-dioxo-[1,2,3]oxathiazolidine-3-carboxylic acid tert-butyl ester [CAS No. 459817-82-4] (0.895 g, 4.01 mmol).

Step E

The title compound, white solid (0.9 g, 88%), MS (ISP) m/z=315.2 [(M+H)⁺], mp 261° C., was prepared in accordance with the general method of intermediate 1, step B, from 7-bromo-1-(2-tert-butoxycarbonylamino-ethyl)-5-chloro-3-methyl-1H-indole-2-carboxylic acid ethyl ester (step D) (1.45 g, 3.25 mmol).

Intermediate 10

7-Bromo-9-chloro-11-methyl-2,3,4,5-tetrahydro-[1,4]diazepino[1,2-a]indol-1-one

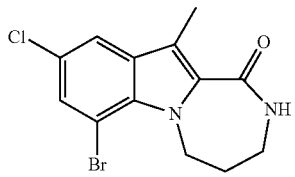

Step A

7-Bromo-1-(3-tert-butoxycarbonylamino-propyl)-5-chloro-3-methyl-1H-indole-2-carboxylic acid methyl ester, light yellow oil (1.4 g, 91%), MS (ISP) m/z=461.3 [(M+H)⁺], was prepared in accordance with the general method of intermediate 1, step A, from methyl 7-bromo-5-chloro-3-methyl-1H-indole-2-carboxylate (intermediate 9, step C)

(1.01 g, 3.34 mmol) and commercially available 2,2-dioxo-2λ'-[1,2,3]oxathiazinane-3-carboxylic acid tert-butyl ester [CAS No. 521267-18-5] (0.95 g, 4.01 mmol).

Step B

The title compound, white solid (0.85 g, 85%), MS (ISP) m/z=329.3 [(M+H)⁺], mp 232° C., was prepared in accordance with the general method of intermediate 1, step B, from 7-bromo-1-(3-tert-butoxycarbonylamino-propyl)-5-chloro-3-methyl-1H-indole-2-carboxylic acid methyl ester (step A) (1.4 g, 3.05 mmol).

Intermediate 11

6-Bromo-8-fluoro-10-methyl-3,4-dihydro-2H-pyrazino[1,2-a]indol-1-one

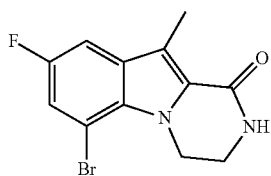 [SMILES: Cc1c2n(c3c(Br)cc(F)cc13)CCNC2=O]

Step A (2-Bromo-4-fluoro-phenyl)-hydrazine, white solid (1.63 g, 89%), MS (ISP) m/z=205.1 [(M+H)⁺], mp 76° C., was prepared in accordance with the general method of intermediate 4, step A, from commercially available 2-bromo-4-fluoro-aniline (1.7 g, 8.95 mmol).

Step B (Z)-2-[(2-bromo-4-fluoro-phenyl)-hydrazono]-butyric acid methyl ester (2.03 g, 85%) as a orange solid, MS (ISP) m/z=303.3 [(M+H)⁺], mp 44° C., was prepared in accordance with the general method of intermediate 9, step B, from (2-bromo-4-fluoro-phenyl)-hydrazine (step A) (1.62 g, 7.9 mmol).

Step C

Methyl 7-bromo-5-fluoro-3-methyl-1H-indole-2-carboxylate, light yellow solid (1.62 g, 85%), MS (ISN) m/z=286.3 [(M−H)⁻], mp 127° C., was prepared in accordance with the general method of intermediate 9, step C, from (Z)-2-[(2-bromo-4-fluoro-phenyl)-hydrazono]-butyric acid methyl ester (step B) (2.02 g, 6.66 mmol).

Step D

7-Bromo-1-(2-tert-butoxycarbonylamino-ethyl)-5-fluoro-3-methyl-1H-indole-2-carboxylic acid ethyl ester, light yellow solid (1.41 g, 98%), MS (ISP) m/z=429.3 [(M+H)⁺], mp 110° C., was prepared in accordance with the general method of intermediate 1, step A, from methyl 7-bromo-5-fluoro-3-methyl-1H-indole-2-carboxylate (step C) (0.956 g, 3.34 mmol) and commercially available 2,2-dioxo-[1,2,3]oxathiazolidine-3-carboxylic acid tert-butyl ester [CAS No. 459817-82-4] (0.895 g, 4.01 mmol).

Step E

The title compound, white solid (0.91 g, 95%), MS (ISP) m/z=299.3 [(M+H)⁺], mp 229° C., was prepared in accordance with the general method of intermediate 1, step B, from 7-bromo-1-(2-tert-butoxycarbonylamino-ethyl)-5-fluoro-3-methyl-1H-indole-2-carboxylic acid ethyl ester (step D) (1.39 g, 3.24 mmol).

Intermediate 12

6-Bromo-1-oxo-1,2,3,4-tetrahydro-pyrazino[1,2-a]indole-8-carbonitrile

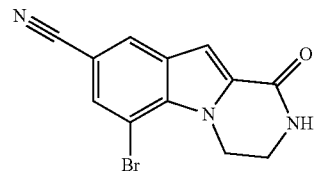 [SMILES: N#Cc1cc(Br)c2c(c1)cc1n2CCNC1=O]

Step A

To a stirred solution of commercially available 4-amino-3-bromo-5-iodobenzonitrile (0.5 g, 1.55 mmol) in THF (7.7 ml) was added Boc-anhydride (0.71 g, 755 µl, 3.25 mmol) and 4-dimethylaminopyridine (18.9 mg, 155 µmol), and the solution was allowed to stir for 3 h at room temperature. The reaction mixture was evaporated and purified by flash chromatography on silica gel (heptane/ethyl acetate 0-50%) to yield a light yellow solid (0.74 g) which was subsequently solved in dichloromethane (2.2 ml) and cooled to 0° C. Afterwards trifluoroacetic acid (318 mg, 215 µl, 2.79 mmol) was added, and the solution was allowed to stir for 3 h at 0° C. Saturated sodium carbonate solution (5 ml) was added and the mixture was extracted with dichloromethane (2×20 ml). The combined organic layers were washed with brine (30 ml), dried (MgSO₄) and evaporated. The crude product (0.69 g) was further purified by flash chromatography on silica gel (heptane/ethyl acetate 0-20%) and crystallization (heptane) to yield (2-bromo-4-cyano-6-iodo-phenyl)-carbamic acid tert-butyl ester (0.42 g, 64%) as an off-white solid, MS (ISN) m/z=421.3 [(M−H)⁻], mp 117.5° C.

Step B

A mixture of (2-bromo-4-cyano-6-iodo-phenyl)-carbamic acid tert-butyl ester (step A) (413 mg, 0.98 mmol), 3,3-diethoxyprop-1-yne (125 mg, 140 µl, 0.98 mmol), triethylamine (395 mg, 544 µl, 3.9 mmol), copper(I)iodide (5.58 mg, 29.3 µmol) and bis(triphenylphosphine)-palladium(II) chloride (34.3 mg, 48.8 µmol) was allowed to stir for 3 h at room temperature. Afterwards 2,3,4,6,7,8,9,10-octahydro-pyrimido[1,2-a]azepine (297 mg, 292 µl, 1.95 mmol) and DMF (1.58 ml) were added, and the reaction mixture was allowed to stir for 17 h at room temperature, poured into water (10 ml) and extracted with ethyl acetate (2×20 ml). The combined organic layers were washed with brine, dried (MgSO₄) and evaporated. The crude product (0.51 g) was further purified by flash chromatography on silica gel (heptane/ethyl acetate 0-20%) to yield 7-bromo-5-cyano-2-diethoxymethyl-indole-1-carboxylic acid tert-butyl ester (0.29 g, 64%) as a light yellow oil, MS (EI) m/z=422 [(M)⁺].

Step C 7-bromo-5-cyano-2-diethoxymethyl-indole-1-carboxylic acid tert-butyl ester (0.29 g, 685 µmol) was solved in THF (2 ml) and cooled to 0° C. Afterwards hydrochloric acid (37%, 1.35 g, 1.14 ml, 13.7 mmol) was added quickly, and the mixture was allowed to stir for 15 min at 0° C. and for 5 h at room temperature. The mixture was cooled (ice bath), saturated sodium carbonate solution (10 ml) was added and the mixture was extracted with ethyl acetate (2×25 ml). The combined organic layers were washed with brine (30 ml), dried (MgSO₄) and evaporated. The crude product (0.18 g) was further purified by flash chromatography on silica gel (heptane/ethyl acetate 0-20%) to yield 7-bromo-2-formyl- 1H-indole-5-carbonitrile (0.17 g, 100%) as an orange solid, MS (ISN) m/z=247.4 [(M−H)⁻], mp 117.5° C.

Step D

To a stirred solution of 7-bromo-2-formyl-1H-indole-5-carbonitrile (0.17 g, 683 μmol) in MeOH (6.03 ml) was added sodium cyanide (167 mg, 3.41 mmol) and manganese dioxide (297 mg, 3.41 mmol) and the reaction mixture was allowed to stir for 17 h at room temperature. The mixture was evaporated, water (20 ml) was added and the mixture was extracted with ethyl acetate (2×15 ml). The combined organic layers were washed with brine, dried (MgSO₄) and evaporated. The crude product (0.11 g) was further purified by flash chromatography on silica gel (heptane/ethyl acetate 0-20%) to yield methyl 7-bromo-5-cyano-1H-indole-2-carboxylate (0.105 g, 55%) as an orange solid, MS (ISN) m/z=279.3 [(M−H)⁻], mp 248° C.

Step E

7-Bromo-1-(2-tert-butoxycarbonylamino-ethyl)-5-cyano-1H-indole-2-carboxylic acid methyl ester, light yellow oil (1.74 g, 95%), MS (ISP) m/z=423.3 [(M+H)⁺], was prepared in accordance with the general method of intermediate 1, step A, from methyl 7-bromo-5-cyano-1H-indole-2-carboxylate (step D) (1.21 g, 4.34 mmol) and commercially available 2,2-dioxo-[1,2,3]oxathiazolidine-3-carboxylic acid tert-butyl ester [CAS No. 459817-82-4] (1.16 g, 5.2 mmol).

Step F

The title compound, light brown solid (0.93 g, 78%), MS (ISP) m/z=288.4 [(M+H)⁺], mp 279° C., was prepared in accordance with the general method of intermediate 1, step B, from 7-bromo-1-(2-tert-butoxycarbonylamino-ethyl)-5-cyano-1H-indole-2-carboxylic acid methyl ester (step A) (1.74 g, 4.12 mmol).

Intermediate 13

6-Bromo-10-methyl-1-oxo-1,2,3,4-tetrahydro-pyrazino[1,2-a]indole-8-carbonitrile

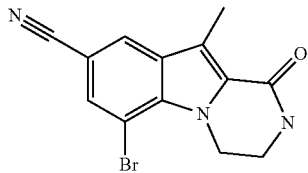 [SMILES: Cc1c2n(c3c(Br)cc(C#N)cc13)CCNC2=O]

Step A (2-Bromo-4-cyano-phenyl)-hydrazine, white solid (5.05 g, 47%), MS (ISN) m/z=210.1 [(M−H)⁻], mp 115° C., was prepared in accordance with the general method of intermediate 4, step A, from commercially available 2-bromo-4-cyano-aniline (10.0 g, 50.8 mmol).

Step B (Z)-2-[(2-bromo-4-cyano-phenyl)-hydrazono]-butyric acid methyl ester (7.33 g, 99%) as a brown solid, MS (ISN) m/z=310.3 [(M−H)⁻], mp 103° C., was prepared in accordance with the general method of intermediate 9, step B, from (2-bromo-4-cyano-phenyl)-hydrazine (step A) (5.04 g, 23.8 mmol).

Step C

Methyl 7-bromo-5-cyano-3-methyl-1H-indole-2-carboxylate, off-white solid (3.44 g, 50%), MS (ISN) m/z=293.4 [(M−H)⁻], mp 248° C., was prepared in accordance with the general method of intermediate 9, step C, from (Z)-2-[(2-bromo-4-cyano-phenyl)-hydrazono]-butyric acid methyl ester (step B) (7.22 g, 23.3 mmol).

Step D

7-Bromo-1-(2-tert-butoxycarbonylamino-ethyl)-5-cyano-3-methyl-1H-indole-2-carboxylic acid ethyl ester, light brown foam (3.88 g, 77%), MS (ISP) m/z=436.5 [(M+H)⁺], was prepared in accordance with the general method of intermediate 1, step A, from methyl 7-bromo-5-cyano-3-methyl-1H-indole-2-carboxylate (step C) (3.40 g, 11.6 mmol) and commercially available 2,2-dioxo-[1,2,3]oxathiazolidine-3-carboxylic acid tert-butyl ester [CAS No. 459817-82-4] (3.11 g, 13.9 mmol).

Step E

The title compound, off-white solid (2.42 g, 91%), MS (ISN) m/z=302.5 [(M−H)⁻], mp 313° C., was prepared in accordance with the general method of intermediate 1, step B, from 7-bromo-1-(2-tert-butoxycarbonylamino-ethyl)-5-cyano-3-methyl-1H-indole-2-carboxylic acid ethyl ester (step D) (3.8 g, 8.71 mmol).

Intermediate 14

7-Bromo-11-methyl-1-oxo-2,3,4,5-tetrahydro-[1,4]diazepino[1,2-a]indole-9-carbonitrile

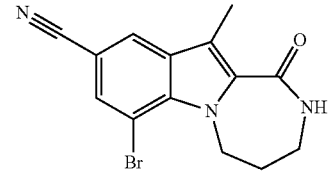 [SMILES: Cc1c2n(c3c(Br)cc(C#N)cc13)CCCNC2=O]

Step A

Methyl 7-bromo-5-cyano-3-methyl-1-[3-[(2-methylpropan-2-yl)-oxycarbonylamino]propyl]-indole-2-carboxylate, white solid (5.61 g, 98%), MS (ISP) m/z=451.3 [(M+H)⁺], mp 136° C., was prepared in accordance with the general method of intermediate 1, step A, from methyl 7-bromo-5-cyano-3-methyl-1H-indole-2-carboxylate (intermediate 16, step C) (3.71 g, 12.7 mmol) and commercially available 2,2-dioxo-2λ'-[1,2,3]oxathiazinane-3-carboxylic acid tert-butyl ester [CAS No. 521267-18-5] (3.6 g, 15.2 mmol).

Step B

The title compound, white solid (2.8 g, 71%), MS (ISP) m/z=318.4 [(M+H)⁺], mp 249° C., was prepared in accordance with the general method of intermediate 1, step B, from methyl 7-bromo-5-cyano-3-methyl-1-[3-[(2-methylpropan-2-yl)-oxycarbonylamino]propyl]-indole-2-carboxylate (step A) (5.61 g, 12.5 mmol).

Intermediate 15

6-Bromo-8-methoxy-3,4-dihydro-2H-pyrazino[1,2-a]indol-1-one

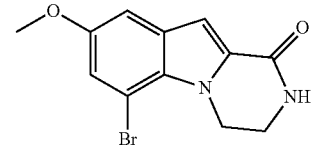 [SMILES: COc1cc(Br)c2c(c1)cc1n2CCNC1=O]

Step A (2-Bromo-4-methoxy-phenyl)-hydrazine, brown solid (4.34 g, 84%), MS (ISN) m/z=216.1 [(M−H)⁻], mp 70° C., was prepared in accordance with the general method of intermediate 4, step A, from commercially available 2-bromo-4-methoxy-aniline (4.79 g, 23.7 mmol).

Step B

Ethyl (2Z)-2-[(2-bromo-4-methoxyphenyl)-hydrazinylidene]-propanoate, brown solid (6.28 g, 99%), MS (ISP) m/z=317.4 [(M+H)⁺], mp 69° C., was prepared in accordance with the general method of intermediate 4, step B, from (2-bromo-4-methoxy-phenyl)-hydrazine (step A) (4.33 g, 15.9 mmol).

Step C

Ethyl 7-bromo-5-methoxy-1H-indole-2-carboxylate, light yellow solid (1.73 g, 31%), MS (ISP) m/z=298.4 [(M+H)⁺], mp 121.5° C., was prepared in accordance with the general method of intermediate 9, step C, from ethyl (2Z)-2-[(2-bromo-4-methoxyphenyl)-hydrazinylidene]-propanoate (step B) (5.9 g, 18.7 mmol).

Step D

Ethyl 7-bromo-5-methoxy-1-{2-[(2-methylpropan-2-yl)-oxycarbonylamino]-ethyl}-indole-2-carboxylate, light yellow oil (1.48 g, 100%), MS (ISP) m/z=442.4 [(M+H)⁺], was prepared in accordance with the general method of intermediate 1, step A, from ethyl 7-bromo-5-methoxy-1H-indole-2-carboxylate (step C) (1.0 g, 3.35 mmol) and commercially available 2,2-dioxo-[1,2,3]oxathiazolidine-3-carboxylic acid tert-butyl ester [CAS No. 459817-82-4] (0.9 g, 4.03 mmol).

Step E

The title compound, off-white solid (0.91 g, 92%), MS (ISP) m/z=295.5 [(M+H)⁺], mp 261° C., was prepared in accordance with the general method of intermediate 1, step B, from ethyl 7-bromo-5-methoxy-1-{2-[2-methylpropan-2-yl)-oxycarbonylamino]-ethyl}-indole-2-carboxylate (step D) (1.48 g, 3.35 mmol).

Intermediate 16

6-Bromo-8-(trifluoromethoxy)-3,4-dihydro-2H-pyrazino[1,2-a]indol-1-one

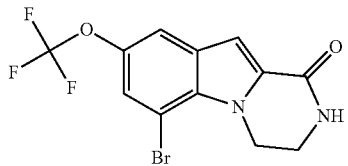 [SMILES: O=C1NCCn2c1cc1cc(OC(F)(F)F)cc(Br)c12]

Step A (2-Bromo-4-trifluoromethoxy-phenyl)-hydrazine, brown oil (2.64 g, 50%), MS (ISP) m/z=271.1 [(M+H)⁺], was prepared in accordance with the general method of intermediate 4, step A, from commercially available 2-bromo-4-trifluoromethoxy-aniline (5.0 g, 19.5 mmol).

Step B

Ethyl (2Z)-2-[2-bromo-4-trifluoromethoxy-phenyl)-hydrazinylidene]-propanoate, light brown solid (3.61 g, 100%), MS (ISP) m/z=369.4 [(M+H)⁺], mp 65° C., was prepared in accordance with the general method of intermediate 4, step B, from (2-bromo-3,4-difluoro-phenyl)-hydrazine (step A) (2.65 g, 9.78 mmol).

Step C

Ethyl 7-bromo-5-trifluoromethoxy-1H-indole-2-carboxylate, off-white solid (2.53 g, 77%), MS (ISN) m/z=350.4 [(M−H)⁻], mp 117° C., was prepared in accordance with the general method of intermediate 4, step C, from ethyl (2Z)-2-[(2-bromo-4-trifluoromethoxy-phenyl)-hydrazinylidene]-propanoate (step B) (3.44 g, 9.32 mmol).

Step D

Ethyl 7-bromo-1-{2-[(2-methylpropan-2-yl)-oxycarbonylamino]-ethyl}-5-(trifluoromethoxy)-indole-2-carboxylate, light yellow oil (1.66 g, 100%), MS (ISP) m/z=496.5 [(M+H)⁺], was prepared in accordance with the general method of intermediate 1, step A, from ethyl 7-bromo-5-trifluoromethoxy-1H-indole-2-carboxylate (step C) (1.18 g, 3.35 mmol) and commercially available 2,2-dioxo-[1,2,3]oxathiazolidine-3-carboxylic acid tert-butyl ester [CAS No. 459817-82-4] (0.9 g, 4.02 mmol).

Step E

The title compound, off-white solid (1.04 g, 89%), MS (ISN) m/z=349.4 [(M+H)⁺], mp 214° C., was prepared in accordance with the general method of intermediate 1, step B, from ethyl 7-bromo-1-{2-[(2-methylpropan-2-yl)-oxycarbonylamino]-ethyl}-5-(trifluoromethoxy)-indole-2-carboxylate (step D) (1.66 g, 3.35 mmol).

Intermediate 17

7-Bromo-1-oxo-2,3,4,5-tetrahydro-[1,4]diazepino[1,2-a]indole-9-carbonitrile

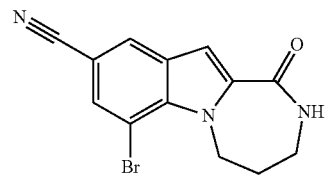 [SMILES: N#Cc1cc(Br)c2c(c1)cc1n2CCCNC1=O]

Step A

Methyl 7-bromo-5-cyano-1-{3-[(2-methylpropan-2-yl)-oxycarbonylamino]-propyl}-indole-2-carboxylate, white solid (1.15 g, 57%), MS (ISP) m/z=438.3 [(M+H)⁺], mp 144° C., was prepared in accordance with the general method of intermediate 1, step A, from methyl 7-bromo-5-cyano-1H-indole-2-carboxylate (intermediate 12, step D) (1.3 g, 4.66 mmol) and commercially available 2,2-dioxo-2λ'-[1,2,3]oxathiazinane-3-carboxylic acid tert-butyl ester [CAS No. 521267-18-5] (1.33 g, 5.59 mmol).

Step B

The title compound, off-white solid (0.65 g, 81%), MS (ISP) m/z=306.3 [(M+H)⁺], mp 256.5° C., was prepared in accordance with the general method of intermediate 1, step B, from methyl 7-bromo-5-cyano-1-{3-[(2-methylpropan-2-yl)-oxycarbonylamino]-propyl}-indole-2-carboxylate (step A) (1.15 g, 2.64 mmol).

EXAMPLE 1

9-Fluoro-7-methyl-2,3,4,5-tetrahydro-[1,4]diazepino[1,2-a]indol-1-one

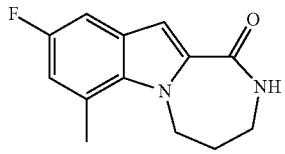

A mixture of 7-bromo-9-fluoro-2,3,4,5-tetrahydro-[1,4]diazepino[1,2-a]indol-1-one (intermediate 2) (74.3 mg, 0.25 mmol), tetrakis triphenylphosphine palladium (28.9 mg, 25.0 μmol) and potassium carbonate (104 mg, 0.75 mmol) in DMF (1.66 ml) was allowed to stir at room temperature for 5 min under argon atmosphere. Then commercially available 2,4,6-trimethyl-1,3,5,2,4,6-trioxatriborinane (71.4 μl, 0.25 mmol) was added and the reaction mixture was allowed to stir at 110° C. for 15 h. Afterwards the reaction mixture was cooled to room temperature, poured into water (20 ml) and extracted with ethyl acetate (2×20 ml). The combined organic layers were washed with brine (1×20 ml), dried (MgSO$_4$) and evaporated. The crude material (90 mg) was purified by flash chromatography on silica gel [dichloromethane-dichloromethane/MeOH 9:1 (20-80%)] and trituration with diethyl ether (1 ml) and heptane (10 ml) to yield the title compound as a white solid (58 mg, 44%), MS (ISP) m/z=233.2 [(M+H)$^+$], mp 198° C.

EXAMPLE 2

8-Fluoro-6-methyl-3,4-dihydro-2H-pyrazino[1,2-a]indol-1-one

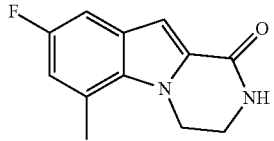 [SMILES: Cc1cc(F)cc2cc3n(c12)CCNC3=O]

The title compound, light yellow solid (44 mg, 81%), MS (ISP) m/z=219.2 [(M+H)$^+$], mp 250.5° C., was prepared in accordance with the general method of example 1 from 6-bromo-8-fluoro-3,4-dihydro-2H-pyrazino[1,2-a]indol-1-one (intermediate 1) (70.8 mg, 0.25 mmol) and commercially available 2,4,6-trimethyl-1,3,5,2,4,6-trioxatriborinane (71.4 μl, 0.25 mmol).

EXAMPLE 3

8-Fluoro-6-isobutyl-10-methyl-3,4-dihydro-2H-pyrazino[1,2-a]indol-1-one

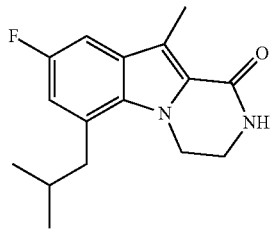

To a mixture of 6-bromo-8-fluoro-10-methyl-3,4-dihydro-2H-pyrazino[1,2-a]indol-1-one (intermediate 11) (74.3 mg, 0.25 mmol) and commercially available isobutylboronic acid (102 mg, 1.0 mmol) in toluene (3 ml), was added at room temperature potassium phosphate, tribasic (106 mg, 0.5 mmol), and the reaction mixture was purged with argon in an ultrasonic bath during 5 min. Afterwards tetrakis(triphenylphosphine)palladium(0) (14.4 mg, 12.5 μmol) was added and the reaction mixture was heated for 5 h under reflux conditions. The reaction mixture was cooled to room temperature, poured into water (20 ml) and extracted with diethyl acetate (2×20 ml). The combined organic layers were washed with brine (20 ml), dried (MgSO$_4$) and evaporated. The crude product (120 mg) was further purified by flash chromatography on silica gel (heptane/ethyl acetate, 20-100%) and crystallization from dichloromethane/heptane to yield the title compound as an off-white solid (33 mg, 48%), MS (ISP) m/z=275.5 [(M+H)$^+$], mp 189° C.

EXAMPLE 4

8-Fluoro-10-methyl-3,4-dihydro-2H-pyrazino[1,2-a]indol-1-one

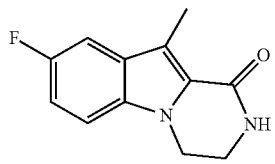 [SMILES: Cc1c2n(c3ccc(F)cc13)CCNC2=O]

The title compound, white solid (16 mg, 29%), MS (ISP) m/z=219.5 [(M+H)$^+$], mp 230° C., was obtained by the reaction of 6-bromo-8-fluoro-10-methyl-3,4-dihydro-2H-pyrazino[1,2-a]indol-1-one (intermediate 11) (74.3 mg, 0.25 mmol) and commercially available isopropylboronic acid (87.9 mg, 1.0 mmol) in accordance with the general method of example 3 instead of the desired product.

EXAMPLE 5

8-Fluoro-6,10-dimethyl-3,4-dihydro-2H-pyrazino[1,2-a]indol-1-one

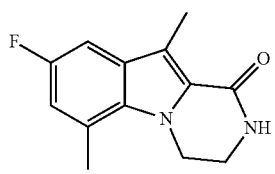 [SMILES: Cc1c2n(c3c(C)cc(F)cc13)CCNC2=O]

The title compound, white solid (34 mg, 59%), MS (ISP) m/z=233.5 [(M+H)$^+$], mp 208° C., was prepared in accordance with the general method of example 1 from 6-bromo-8-fluoro-10-methyl-3,4-dihydro-2H-pyrazino[1,2-a]indol-1-one (intermediate 11) (74.3 mg, 0.25 mmol) and commercially available 2,4,6-trimethyl-1,3,5,2,4,6-trioxatriborinane (71.4 μl, 0.25 mmol).

EXAMPLE 6

8-Fluoro-10-methyl-6-morpholin-4-yl-3,4-dihydro-2H-pyrazino[1,2-a]indol-1-one

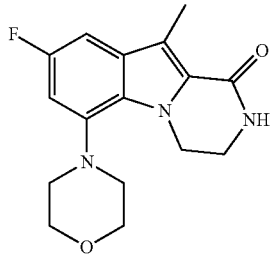 [SMILES: Cc1c2n(c3c(N4CCOCC4)cc(F)cc13)CCNC2=O]

A mixture of 6-bromo-8-fluoro-10-methyl-3,4-dihydro-2H-pyrazino[1,2-a]indol-1-one (intermediate 11) (149 mg, 0.5 mmol), sodium tert-butoxide (72.1 mg, 0.75 mmol), (R)-2,2'-bis(diphenylphosphino)-1,1'-binaphthyl (24.9 mg, 40.0 µmol), tris(dibenzylideneacetone)-dipalladium(0) (18.3 mg, 20.0 µmol) and morpholine (87.1 mg, 87.1 µl, 1.0 mmol) in toluene (2 ml) was allowed to stir for 21 h at 100° C. Afterwards, the reaction mixture was filtered through Dicalite, the collected solid was washed with diethylacetate and the organic phase was evaporated. The crude product (140 mg) was purified by flash chromatography on silica gel (dichloromethane/MeOH, 0-20%) to yield the title compound as a white solid (22 mg, 14%), MS (ISP) m/z=304.6 [(M+H)$^+$], mp 226° C.

EXAMPLE 7

8-Chloro-6,10-dimethyl-3,4-dihydro-2H-pyrazino[1,2-a]indol-1-one

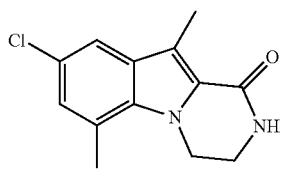 [SMILES: Cc1c2n(c3c(C)cc(Cl)cc13)CCNC2=O]

The title compound, white solid (43 mg, 69%), MS (ISP) m/z=249.4 [(M+H)$^+$], mp 251° C., was prepared in accordance with the general method of example 1 from 7-bromo-9-chloro-11-methyl-2,3,4,5-tetrahydro-[1,4]diazepino[1,2-a]indol-1-one (intermediate 9) (78.4 mg, 0.25 mmol) and commercially available 2,4,6-trimethyl-1,3,5,2,4,6-trioxatriborinane (71.4 µl, 0.25 mmol).

EXAMPLE 8

6-Ethyl-8-fluoro-10-methyl-3,4-dihydro-2H-pyrazino[1,2-a]indol-1-one

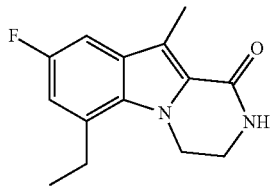

The title compound, white solid (35 mg, 57%), MS (ISP) m/z=247.5 [(M+H)$^+$], mp 177° C., was prepared in accordance with the general method of example 3 from 6-bromo-8-fluoro-10-methyl-3,4-dihydro-2H-pyrazino[1,2-a]indol-1-one (intermediate 11) (74.3 mg, 0.25 mmol) and commercially available ethylboronic acid (73.9 mg, 1.0 mmol).

EXAMPLE 9

6-(1,1-Dioxo-1λ$^6$-thiomorpholin-4-yl)-8-fluoro-10-methyl-3,4-dihydro-2H-pyrazino[1,2-a]indol-1-one

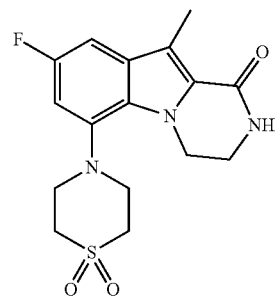

The title compound, white solid (18 mg, 10%), MS (ISP) m/z=352.5 [(M+H)$^+$], mp 387° C., was prepared in accordance with the general method of example 6 from 6-bromo-8-fluoro-10-methyl-3,4-dihydro-2H-pyrazino[1,2-a]indol-1-one (intermediate 11) (149 mg, 0.50 mmol) and commercially available thiomorpholine 1,1-dioxide (135 mg, 1.0 mmol).

EXAMPLE 10

8-Chloro-6-ethyl-10-methyl-3,4-dihydro-2H-pyrazino[1,2-a]indol-1-one

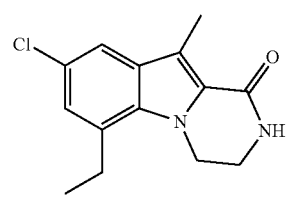 [SMILES: CCc1cc(Cl)cc2c(C)c3n(c12)CCNC3=O]

The title compound, off-white solid (40 mg, 61%), MS (ISP) m/z=263.5 [(M+H)$^+$], mp 191° C., was prepared in accordance with the general method of example 3 from 7-bromo-9-chloro-11-methyl-2,3,4,5-tetrahydro-[1,4]diazepino[1,2-a]indol-1-one (intermediate 9) (78.4 mg, 0.25 mmol) and commercially available ethylboronic acid (22.2 mg, 0.3 mmol).

EXAMPLE 11

6-Allyl-8-fluoro-10-methyl-3,4-dihydro-2H-pyrazino[1,2-a]indol-1-one

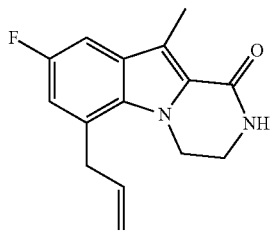 [SMILES: C=CCc1cc(F)cc2c(C)c3n(c12)CCNC3=O]

The title compound, white solid (43 mg, 67%), MS (ISP) m/z=259.4 [(M+H)+], mp 172° C., was prepared in accordance with the general method of example 3 from 6-bromo-8-fluoro-10-methyl-3,4-dihydro-2H-pyrazino[1,2-a]indol-1-one (intermediate 11) (74.3 mg, 0.25 mmol) and commercially available allylboronic acid (85.9 mg, 1.0 mmol).

EXAMPLE 12

8-Fluoro-10-methyl-6-(3-methyl-butyl)-3,4-dihydro-2H-pyrazino[1,2-a]indol-1-one

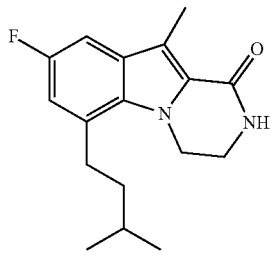 [SMILES: Cc1c2n(c3c(CCC(C)C)cc(F)cc13)CCNC2=O]

The title compound, white solid (47 mg, 65%), MS (ISP) m/z=289.5 [(M+H)+], mp 161° C., was prepared in accordance with the general method of example 3 from 6-bromo-8-fluoro-10-methyl-3,4-dihydro-2H-pyrazino[1,2-a]indol-1-one (intermediate 11) (74.3 mg, 0.25 mmol) and commercially available isopentylboronic acid (116 mg, 1.0 mmol).

EXAMPLE 13

4-(8-Fluoro-10-methyl-1-oxo-1,2,3,4-tetrahydro-pyrazino[1,2-a]indol-6-yl)-butyronitrile

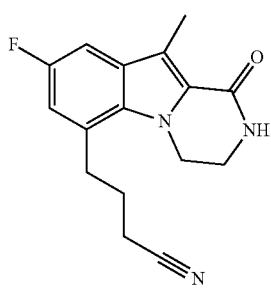 [SMILES: Cc1c2n(c3c(CCCC#N)cc(F)cc13)CCNC2=O]

The title compound, white solid (20 mg, 28%), MS (ISP) m/z=286.4 [(M+H)+], mp 194° C., was prepared in accordance with the general method of example 3 from 6-bromo-8-fluoro-10-methyl-3,4-dihydro-2H-pyrazino[1,2-a]indol-1-one (intermediate 11) (74.3 mg, 0.25 mmol) and commercially available 4-(4,4,5,5-tetramethyl-1,3,2-dioxaborolan-2-yl)butanenitrile (195 mg, 1.0 mmol).

EXAMPLE 14

8-Chloro-6-isobutyl-10-methyl-3,4-dihydro-2H-pyrazino[1,2-a]indol-1-one

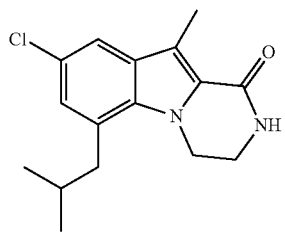 [SMILES: Cc1c2n(c3c(CC(C)C)cc(Cl)cc13)CCNC2=O]

The title compound, white solid (32 mg, 44%), MS (ISP) m/z=291.6 [(M+H)+], mp 199° C., was prepared in accordance with the general method of example 3 from 7-bromo-9-chloro-11-methyl-2,3,4,5-tetrahydro-[1,4]diazepino[1,2-a]indol-1-one (intermediate 9) (78.4 mg, 0.25 mmol) and commercially available isobutylboronic acid (102 mg, 1.0 mmol).

EXAMPLE 15

8-Fluoro-6-(4-fluoro-benzyl)-10-methyl-3,4-dihydro-2H-pyrazino[1,2-a]indol-1-one

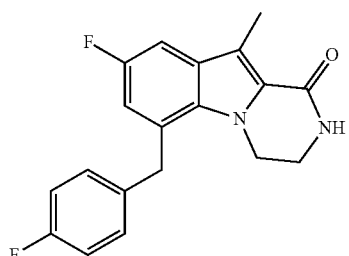

The title compound, white solid (58 mg, 71%), MS (ISP) m/z=327.5 [(M+H)+], mp 178° C., was prepared in accordance with the general method of example 3 from 6-bromo-8-fluoro-10-methyl-3,4-dihydro-2H-pyrazino[1,2-a]indol-1-one (intermediate 11) (74.3 mg, 0.25 mmol) and commercially available 2-(4-fluorobenzyl)-4,4,5,5-tetramethyl-1,3,2-dioxaborolane (76.7 mg, 0.325 mmol).

EXAMPLE 16

8-Fluoro-10-methyl-6-(2-oxa-6-aza-spiro[3.3]hept-6-yl)-3,4-dihydro-2H-pyrazino[1,2-a]indol-1-one

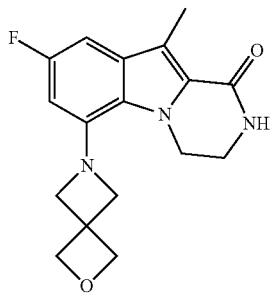 [SMILES: Cc1c2n(c3c(N4CC5(COC5)C4)cc(F)cc13)CCNC2=O]

The title compound, off-white solid (20 mg, 13%), MS (ISP) m/z=316.5 [(M+H)+], mp 237° C., was prepared in accordance with the general method of example 6 from 6-bromo-8-fluoro-10-methyl-3,4-dihydro-2H-pyrazino[1,2-a]indol-1-one (intermediate 11) (149 mg, 0.50 mmol) and commercially available 2-oxa-6-azaspiro[3.3]heptane oxalate (189 mg, 1.0 mmol).

EXAMPLE 17

8-Chloro-6-(1,1-dioxo-1λ$^6$-thiomorpholin-4-yl)-10-methyl-3,4-dihydro-2H-pyrazino[1,2-a]indol-1-one

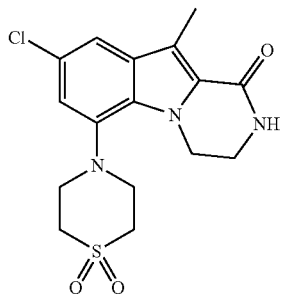 [SMILES: Cc1c2n(c3c(N4CCS(=O)(=O)CC4)cc(Cl)cc13)CCNC2=O]

The title compound, white solid (8 mg, 4%), MS (ISP) m/z=368.5 [(M+H)+], mp 386° C., was prepared in accordance with the general method of example 6 from 7-bromo-9-chloro-11-methyl-2,3,4,5-tetrahydro-[1,4]diazepino[1,2-a]indol-1-one (intermediate 9) (157 mg, 0.5 mmol) and commercially available thiomorpholine 1,1-dioxide (135 mg, 1.0 mmol).

EXAMPLE 18

8-Chloro-10-methyl-6-morpholin-4-yl-3,4-dihydro-2H-pyrazino[1,2-a]indol-1-one

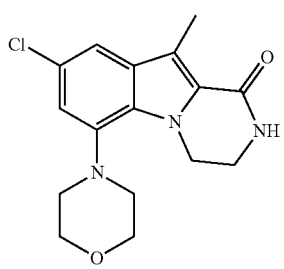 [SMILES: Cc1c2n(c3c(N4CCOCC4)cc(Cl)cc13)CCNC2=O]

The title compound, white solid (6 mg, 4%), MS (ISP) m/z=320.6 [(M+H)+], mp 207° C., was prepared in accordance with the general method of example 6 from 7-bromo-9-chloro-11-methyl-2,3,4,5-tetrahydro-[1,4]diazepino[1,2-a]indol-1-one (intermediate 9) (157 mg, 0.5 mmol) and commercially available morpholine (87.1 mg, 87.1 μl, 1.0 mmol).

EXAMPLE 19

6-(1,1-Dioxo-1λ$^6$-thiomorpholin-4-yl)-10-methyl-1-oxo-1,2,3,4-tetrahydro-pyrazino[1,2-a]indole-8-carbonitrile

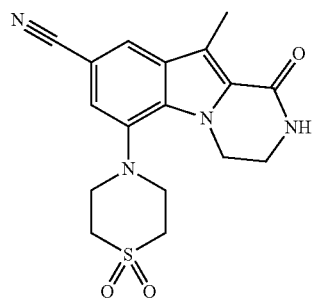 [SMILES: Cc1c2n(c3c(N4CCS(=O)(=O)CC4)cc(C#N)cc13)CCNC2=O]

The title compound, white solid (10 mg, 6%), MS (ISP) m/z=359.5 [(M+H)+], mp 400° C., was prepared in accordance with the general method of example 6 from 6-bromo-10-methyl-1-oxo-1,2,3,4-tetrahydro-pyrazino[1,2-a]indole-8-carbonitrile (intermediate 13) (152 mg, 0.50 mmol) and commercially available thiomorpholine 1,1-dioxide (135 mg, 1.0 mmol).

EXAMPLE 20

6-Ethynyl-8-fluoro-10-methyl-3,4-dihydro-2H-pyrazino[1,2-a]indol-1-one

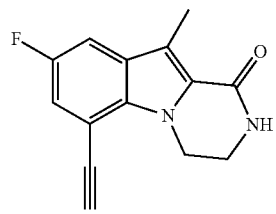 [SMILES: C#Cc1cc(F)cc2c(C)c3n(c12)CCNC3=O]

Step A

To a stirred mixture of triphenylphosphine (17.7 mg, 67.3 μmol), palladium(II)acetate (7.56 mg, 33.7 μmol) and copper(I)iodide (8.01 mg, 42.1 μmol) in tetrahydrofurane (1 ml), was added at room temperature triethylamine (579 mg, 797 μl, 5.72 mmol), 6-bromo-8-fluoro-10-methyl-3,4-dihydro-2H-pyrazino[1,2-a]indol-1-one (intermediate 11) (0.25 g, 0.84 mmol) and commercially available ethynyltrimethylsilane (124 mg, 175 μl, 1.26 mmol), and the reaction mixture was allowed to stir at 70° C. for 23 h. The reaction mixture was poured into water (30 ml) and extracted with ethyl acetate (2×40 ml). The combined organic layers were washed with brine (30 ml), dried (MgSO$_4$) and evaporated. The crude product (150 mg dark brown solid) was further purified by flash chromatography on silica gel (heptane/ethyl acetate 50-100%) to yield 8-fluoro-10-methyl-6-trimethylsilanylethynyl-3,4-dihydro-2H-pyrazino[1,2-a]indol-1-one as a brown solid (43 mg, 16%), MS (ISP) m/z=315.5 [(M+H)⁺], mp 194° C.

Step B

To a stirred solution of 8-fluoro-10-methyl-6-trimethylsilanylethynyl-3,4-dihydro-2H-pyrazino[1,2-c]indol-1-one (Step A) (43 mg, 137 μmol) in methanol (1 ml) and tetrahydrofurane (1 ml) was added at 0° C. potassium carbonate (9.45 mg, 68.4 μmol) and the reaction mixture was allowed to stir at 0° C. for 2 h. The reaction mixture was diluted with tetrahydrofurane (5 ml), filtered and evaporated. The crude product was purified by flash chromatography on silica gel (diethyl acetate) and trituration (diethyl ether) to yield the title compound as a light brown solid (21 mg, 63%), MS (ISP) m/z=243.5 [(M+H)⁺], mp 259° C.

EXAMPLE 21

6-Isobutyl-1-oxo-1,2,3,4-tetrahydro-pyrazino[1,2-a]indole-8-carbonitrile

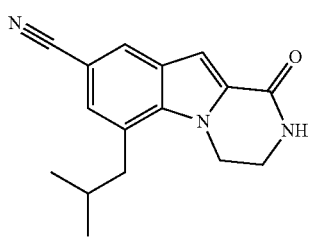 [SMILES: CC(C)Cc1cc(C#N)cc2cc3n(c12)CCNC3=O]

The title compound, off-white solid (78 mg, 58%), MS (ISP) m/z=268.5 [(M+H)⁺], mp 260.5° C., was prepared in accordance with the general method of example 3 from 6-bromo-1-oxo-1,2,3,4-tetrahydro-pyrazino[1,2-a]indole-8-carbonitrile (intermediate 12) (145 mg, 0.5 mmol) and commercially available isobutylboronic acid (204 mg, 2.0 mmol).

EXAMPLE 22

9-Fluoro-7-isobutyl-2,3,4,5-tetrahydro-[1,4]diazepino[1,2-a]indol-1-one

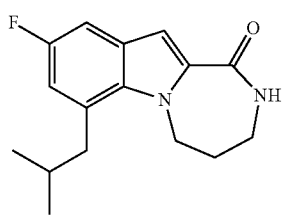 [SMILES: CC(C)Cc1cc(F)cc2cc3n(c12)CCCNC3=O]

The title compound, white solid (33 mg, 48%), MS (ISP) m/z=275.6 [(M+H)⁺], mp 157° C., was prepared in accordance with the general method of example 3 from 7-bromo-9-fluoro-2,3,4,5-tetrahydro-[1,4]diazepino[1,2-a]indol-1-one (intermediate 2) (74.3 mg, 0.25 mmol) and commercially available isobutylboronic acid (38.2 mg, 0.375 mmol).

EXAMPLE 23

8-Fluoro-6-(2-methylpropyl)-3,4-dihydro-2H-pyrazino[1,2-a]indol-1-one

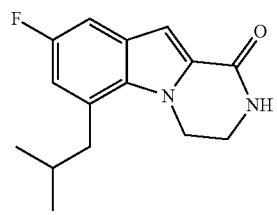 [SMILES: CC(C)Cc1cc(F)cc2cc3n(c12)CCNC3=O]

The title compound, white solid (33 mg, 51%), MS (ISP) m/z=261.5 [(M+H)⁺], mp 229° C., was prepared in accordance with the general method of example 3 from 6-bromo-8-fluoro-3,4-dihydro-2H-pyrazino[1,2-a]indol-1-one (intermediate 1) (70.8 mg, 0.25 mmol) and commercially available isobutylboronic acid (38.2 mg, 0.375 mmol).

EXAMPLE 24

8-Fluoro-10-methyl-6-(2,2,2-trifluoroethoxy)-3,4-dihydro-2H-pyrazino[1,2-a]indol-1-one

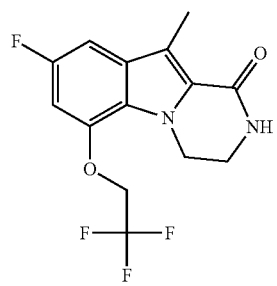 [SMILES: Cc1c2n(c3c(OCC(F)(F)F)cc(F)cc13)CCNC2=O]

A mixture of 6-bromo-8-fluoro-10-methyl-3,4-dihydro-2H-pyrazino[1,2-a]indol-1-one (intermediate 11) (149 mg, 0.5 mmol), copper(I)iodide (9.52 mg, 50.0 μmol), cesium carbonate (228 mg, 0.7 mmol), ethyl 2-cyclohexanonecarboxylate (18.9 mg, 17.7 μl, 0.1 mmol) and 2,2,2-trifluoroethanol (700 mg, 506 μl, 7.0 mmol) was heated in a sealed microwave tube for 24 h at 110° C. The reaction mixture was cooled to room temperature, filtered (Dicalite) and washed with ethyl acetate. The organic layer was evaporated, and the crude product was purified by flash chromatography on silica gel (heptane/ethyl acetate 20-80%) and crystallization (dichloromethane/methanol/heptane) to yield the title compound as a white solid (31 mg, 20%), MS (ISP) m/z=317.4 [(M+H)⁺], mp 239° C.

EXAMPLE 25

9-Chloro-7-(2-methylpropyl)-2,3,4,5-tetrahydro-[1,4]diazepino[1,2-a]indol-1-one

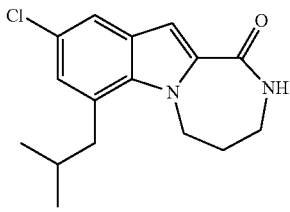 [SMILES: CC(C)Cc1cc(Cl)cc2cc3n(c12)CCCNC3=O]

The title compound, off-white solid (28 mg, 39%), MS (ISP) m/z=291.4 [(M+H)$^+$], mp 186° C., was prepared in accordance with the general method of example 3 from 7-bromo-9-chloro-2,3,4,5-tetrahydro-[1,4]diazepino[1,2-a]indol-1-one (intermediate 5) (78.4 mg, 0.25 mmol) and commercially available isobutylboronic acid (38.2 mg, 0.375 mmol).

EXAMPLE 26

8-Chloro-6-(2-methylpropyl)-3,4-dihydro-2H-pyrazino[1,2-a]indol-1-one

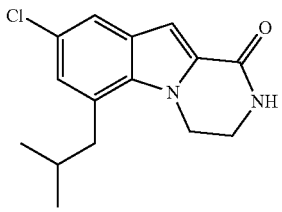

The title compound, white solid (32 mg, 46%), MS (ISP) m/z=277.4 [(M+H)$^+$], mp 236° C., was prepared in accordance with the general method of example 3 from 6-bromo-8-chloro-3,4-dihydro-2H-pyrazino[1,2-a]indol-1-one (intermediate 6) (74.9 mg, 0.25 mmol) and commercially available isobutylboronic acid (38.2 mg, 0.375 mmol).

EXAMPLE 27

8-Chloro-6-methyl-3,4-dihydro-2H-pyrazino[1,2-a]indol-1-one

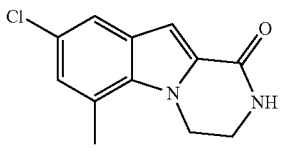 [SMILES: Cc1cc(Cl)cc2cc3n(c12)CCNC3=O]

The title compound, white solid (22 mg, 37%), MS (ISP) m/z=235.5 [(M+H)$^+$], mp 263° C., was prepared in accordance with the general method of example 1 from 6-bromo-8-chloro-3,4-dihydro-2H-pyrazino[1,2-a]indol-1-one (intermediate 6) (74.9 mg, 0.25 mmol) and commercially available 2,4,6-trimethyl-1,3,5,2,4,6-trioxatriborinane (71.4 µl, 0.25 mmol).

EXAMPLE 28

9-Chloro-7-methyl-2,3,4,5-tetrahydro-[1,4]diazepino[1,2-a]indol-1-one

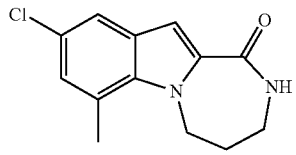 [SMILES: Cc1cc(Cl)cc2cc3n(c12)CCCNC3=O]

The title compound, white solid (21 mg, 34%), MS (ISP) m/z=249.4 [(M+H)$^+$], mp 207° C., was prepared in accordance with the general method of example 1 from 7-bromo-9-chloro-2,3,4,5-tetrahydro-[1,4]diazepino[1,2-a]indol-1-one (intermediate 5) (78.4 mg, 0.25 mmol) and commercially available 2,4,6-trimethyl-1,3,5,2,4,6-trioxatriborinane (71.4 µl, 0.25 mmol).

EXAMPLE 29

8-Fluoro-10-methyl-1-oxo-3,4-dihydro-2H-pyrazino[1,2-a]indole-6-carbonitrile

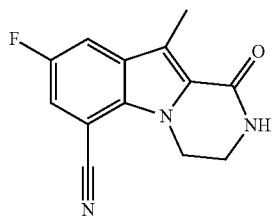 [SMILES: Cc1c2n(c3c(C#N)cc(F)cc13)CCNC2=O]

To a solution of 6-bromo-8-fluoro-10-methyl-3,4-dihydro-2H-pyrazino[1,2-a]indol-1-one (intermediate 11) (0.1 g, 337 µmol) in DMF (1.5 ml) zinc cyanide (45.9 mg, 390 µmol) was added at room temperature, and the reaction mixture was purged with argon for 5 min in an ultrasonic bath. Afterwards tetrakis(triphenylphosphine)palladium(0) (26 mg, 22.5 µmol) was added and the reaction mixture was allowed to stir for 90 min at 90° C. The reaction mixture was poured into 2M potassium carbonate solution (20 ml) and extracted with ethyl acetate (2×40 ml). The combined organic layers were washed with brine (20 ml), dried (MgSO$_4$) and evaporated. The crude product was further purified by flash chromatography on silica gel (ethyl acetate) and trituration (diethyl ether) to yield the title compound as a white solid (67 mg, 82%), MS (ISP) m/z=244.4 [(M+H)$^+$], mp 265° C.

EXAMPLE 30

10-Methyl-1-oxo-6-(trifluoromethoxy)-3,4-dihydro-2H-pyrazino[1,2-a]indole-8-carbonitrile

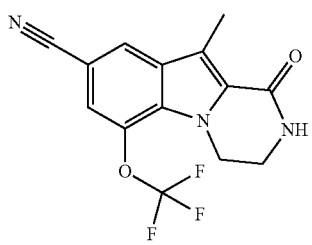 [SMILES: Cc1c2n(c3c(OC(F)(F)F)cc(C#N)cc13)CCNC2=O]

Step A

4-Hydrazinyl-3-trifluoromethoxy-benzonitrile, light green solid (0.8 g, 75%), MS (ISP) m/z=218.2 [(M+H)+], mp 127° C., was prepared in accordance with the general method of intermediate 4, step A, from commercially available 4-amino-3-trifluoromethoxy-benzonitrile (1.0 g, 4.95 mmol).

Step B

Methyl (2Z)-2-[4-cyano-2-trifluoromethoxy-phenyl)-hydrazinylidene]-butanoate (1.14 g, 98%) as a brown oil, MS (ISP) m/z=316.4 [(M+H)+], was prepared in accordance with the general method of intermediate 9, step B, from 4-hydrazinyl-3-trifluoromethoxy-benzonitrile (step A) (0.8 g, 3.68 mmol).

Step C

Methyl 5-cyano-3-methyl-7-(trifluoromethoxy)-1H-indole-2-carboxylate, light yellow solid (0.46 g, 43%), MS (ISN) m/z=299.5 [(M+H)+], mp 184° C., was prepared in accordance with the general method of intermediate 9, step C, from methyl (2Z)-2-[4-cyano-2-trifluoromethoxy-phenyl)-hydrazinylidene]-butanoate (step B) (1.14 g, 3.62 mmol).

Step D

Methyl 5-cyano-3-methyl-1-{2-[(2-methylpropan-2-yl)-oxycarbonylamino]-ethyl}-7-trifluoromethoxy-indole-2-carboxylate, light yellow solid (0.45 g, 92%), MS (ISP) m/z=442.5 [(M+H)+], mp 133° C., was prepared in accordance with the general method of intermediate 1, step A, from methyl 5-cyano-3-methyl-7-(trifluoromethoxy)-1H-indole-2-carboxylate (step C) (0.33 g, 1.11 mmol) and commercially available 2,2-dioxo-[1,2,3]oxathiazolidine-3-carboxylic acid tert-butyl ester [CAS No. 459817-82-4] (0.3 g, 1.33 mmol).

Step E

The title compound, white solid (245 mg, 79%), MS (ISP) m/z=310.5 [(M+H)+], mp 253° C., was prepared in accordance with the general method of intermediate 1, step B, from methyl 5-cyano-3-methyl-1-{2-[(2-methylpropan-2-yl)-oxycarbonylamino]-ethyl}-7-trifluoromethoxy-indole-2-carboxylate (step D) (445 mg, 1.01 mmol).

EXAMPLE 31

8-Methyl-6-(2-methylpropyl)-3,4-dihydro-2H-pyrazino[1,2-a]indol-1-one

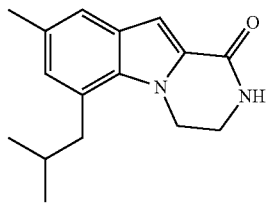 [SMILES: Cc1cc(CC(C)C)c2c(c1)cc1n2CCNC1=O]

The title compound, white solid (39 mg, 61%), MS (ISP) m/z=257.6 [(M+H)+], mp 182° C., was prepared in accordance with the general method of example 3 from 6-bromo-8-methyl-3,4-dihydro-2H-pyrazino[1,2-a]indol-1-one (intermediate 7) (69.8 mg, 0.25 mmol) and commercially available isobutylboronic acid (38.2 mg, 0.375 mmol).

EXAMPLE 32

9-Methyl-7-(2-methylpropyl)-2,3,4,5-tetrahydro-[1,4]diazepino[1,2-a]indol-1-one

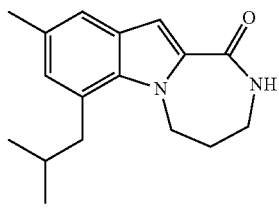

The title compound, white solid (40 mg, 59%), MS (ISP) m/z=271.6 [(M+H)+], mp 160° C., was prepared in accordance with the general method of example 3 from 7-bromo-9-methyl-2,3,4,5-tetrahydro-[1,4]diazepino[1,2-a]indol-1-one (intermediate 8) (73.3 mg, 0.25 mmol) and commercially available isobutylboronic acid (38.2 mg, 0.375 mmol).

EXAMPLE 33

6,8-Dimethyl-3,4-dihydro-2H-pyrazino[1,2-a]indol-1-one

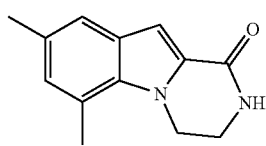 [SMILES: Cc1cc(C)c2c(c1)cc1n2CCNC1=O]

The title compound, white solid (21 mg, 39%), MS (ISP) m/z=215.5 [(M+H)+], mp 253° C., was prepared in accordance with the general method of example 1 from 6-bromo-8-methyl-3,4-dihydro-2H-pyrazino[1,2-a]indol-1-one (intermediate 7) (69.8 mg, 0.25 mmol) and commercially available 2,4,6-trimethyl-1,3,5,2,4,6-trioxatriborinane (71.4 µl, 0.25 mmol).

EXAMPLE 34

11-Methyl-7-(2-methylpropyl)-1-oxo-2,3,4,5-tetrahydro-[1,4]diazepino[1,2-a]indole-9-carbonitrile

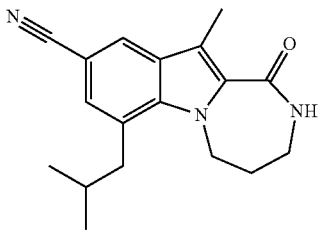

The title compound, white solid (41 mg, 56%), MS (ISP) m/z=296.5 [(M+H)⁺], mp 235° C., was prepared in accordance with the general method of example 3 from 7-bromo-11-methyl-1-oxo-2,3,4,5-tetrahydro-[1,4]diazepino[1,2-a]indole-9-carbonitrile (intermediate 14) (79.5 mg, 0.25 mmol) and commercially available isobutylboronic acid (38.2 mg, 0.375 mmol).

EXAMPLE 35

7,11-Dimethyl-1-oxo-2,3,4,5-tetrahydro-[1,4]diazepino[1,2-a]indole-9-carbonitrile

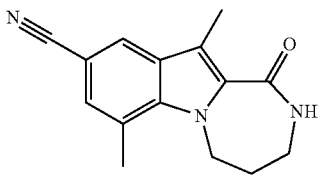 [SMILES: Cc1c2n(c3c(C)cc(C#N)cc13)CCCNC2=O]

The title compound, white solid (53 mg, 84%), MS (ISP) m/z=254.5 [(M+H)⁺], mp 255° C., was prepared in accordance with the general method of example 1 from 7-bromo-11-methyl-1-oxo-2,3,4,5-tetrahydro-[1,4]diazepino[1,2-a]indole-9-carbonitrile (intermediate 14) (79.5 mg, 0.25 mmol) and commercially available 2,4,6-trimethyl-1,3,5,2,4,6-trioxatriborinane (85.7 µl, 0.30 mmol).

EXAMPLE 36

8-Methoxy-6-(2-methylpropyl)-3,4-dihydro-2H-pyrazino[1,2-a]indol-1-one

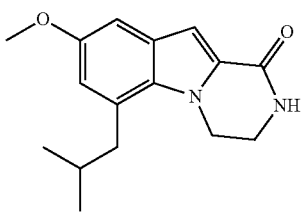 [SMILES: COc1cc(CC(C)C)c2c(c1)cc1n2CCNC1=O]

The title compound, white solid (35 mg, 51%), MS (ISP) m/z=273.5 [(M+H)⁺], mp 175° C., was prepared in accordance with the general method of example 3 from 6-bromo-8-methoxy-3,4-dihydro-2H-pyrazino[1,2-a]indol-1-one (intermediate 15) (73.8 mg, 0.25 mmol) and commercially available isobutylboronic acid (38.2 mg, 0.375 mmol).

EXAMPLE 37

6-(2-Methylpropyl)-8-(trifluoromethoxy)-3,4-dihydro-2H-pyrazino[1,2-a]indol-1-one

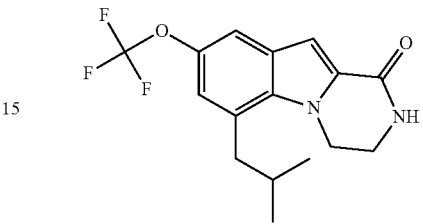

The title compound, white solid (41 mg, 50%), MS (ISP) m/z=327.4 [(M+H)⁺], mp 166° C., was prepared in accordance with the general method of example 3 from 6-bromo-8-(trifluoromethoxy)-3,4-dihydro-2H-pyrazino[1,2-a]indol-1-one (intermediate 16) (87.3 mg, 0.25 mmol) and commercially available isobutylboronic acid (38.2 mg, 0.375 mmol).

EXAMPLE 38

9-Chloro-11-methyl-7-(2-methylpropyl)-2,3,4,5-tetrahydro-[1,4]diazepino[1,2-a]indol-1-one

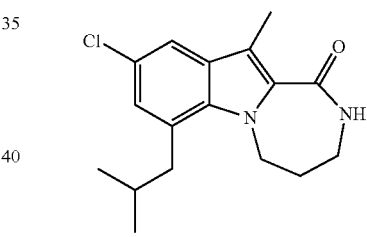

The title compound, white solid (42 mg, 55%), MS (ISP) m/z=305.6 [(M+H)⁺], mp 176° C., was prepared in accordance with the general method of example 3 from 7-bromo-9-chloro-11-methyl-2,3,4,5-tetrahydro-[1,4]diazepino[1,2-a]indol-1-one (intermediate 10) (81.9 mg, 0.25 mmol) and commercially available isobutylboronic acid (38.2 mg, 0.375 mmol).

EXAMPLE 39

9-Chloro-7,11-dimethyl-2,3,4,5-tetrahydro-[1,4]diazepino[1,2-a]indol-1-one

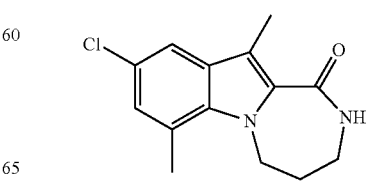

The title compound, white solid (49 mg, 75%), MS (ISP) m/z=263.5 [(M+H)+], mp 198° C., was prepared in accordance with the general method of example 1 from 7-bromo-9-chloro-11-methyl-2,3,4,5-tetrahydro-[1,4]diazepino[1,2-a]indol-1-one (intermediate 10) (81.9 mg, 0.25 mmol) and commercially available 2,4,6-trimethyl-1,3,5,2,4,6-trioxatriborinane (85.7 μl, 0.30 mmol).

EXAMPLE 40

7-(2-Methylpropyl)-1-oxo-2,3,4,5-tetrahydro-[1,4]diazepino[1,2-a]indole-9-carbonitrile

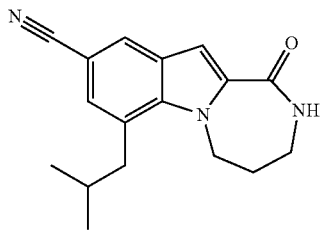 [SMILES: CC(C)Cc1cc(C#N)cc2cc3n(c12)CCCNC3=O]

The title compound, light yellow solid (38 mg, 54%), MS (ISP) m/z=282.5 [(M+H)+], mp 199° C., was prepared in accordance with the general method of example 3 from 7-bromo-1-oxo-2,3,4,5-tetrahydro-[1,4]diazepino[1,2-a]indole-9-carbonitrile (intermediate 17) (76.0 mg, 0.25 mmol) and commercially available isobutylboronic acid (38.2 mg, 0.375 mmol).

EXAMPLE 41

10-Methyl-6-morpholin-4-yl-1-oxo-3,4-dihydro-2H-pyrazino[1,2-a]indole-8-carbonitrile

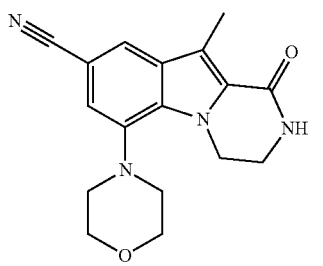 [SMILES: Cc1c2n(c3c(N4CCOCC4)cc(C#N)cc13)CCNC2=O]

The title compound, light yellow solid (4 mg, 4%), MS (ISP) m/z=311.5 [(M+H)+], mp 276° C., was prepared in accordance with the general method of example 6 from 6-bromo-10-methyl-1-oxo-1,2,3,4-tetrahydro-pyrazino[1,2-a]indole-8-carbonitrile (intermediate 13) (100 mg, 0.33 mmol) and commercially available morpholine (31.5 mg, 31.1 μl, 0.36 mmol).

EXAMPLE 42

7-(1,1-Dioxo-1,4-thiazinan-4-yl)-11-methyl-1-oxo-2,3,4,5-tetrahydro-[1,4]diazepino[1,2-a]indole-9-carbonitrile

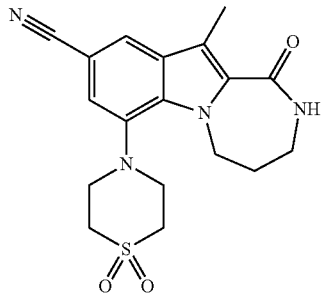 [SMILES: Cc1c2n(c3c(N4CCS(=O)(=O)CC4)cc(C#N)cc13)CCCNC2=O]

The title compound, off-white solid (15 mg, 8%), MS (ISP) m/z=373.5 [(M+H)+], mp 393° C., was prepared in accordance with the general method of example 6 from 7-bromo-11-methyl-1-oxo-2,3,4,5-tetrahydro-[1,4]diazepino[1,2-a]indole-9-carbonitrile (intermediate 14) (159 mg, 0.5 mmol) and commercially available thiomorpholine 1,1-dioxide (135 mg, 1.0 mmol).

EXAMPLE 43

7-(1,1-Dioxo-1,4-thiazinan-4-yl)-1-oxo-2,3,4,5-tetrahydro-[1,4]diazepino[1,2-a]indole-9-carbonitrile

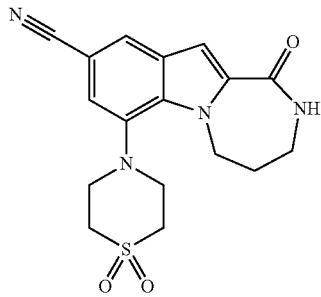 [SMILES: N#Cc1cc(N2CCS(=O)(=O)CC2)c2c(c1)cc1n2CCCNC1=O]

The title compound, off-white solid (13 mg, 7%), MS (ISP) m/z=359.5 [(M+H)+], mp 404.5° C., was prepared in accordance with the general method of example 6 from 7-bromo-1-oxo-2,3,4,5-tetrahydro-[1,4]diazepino[1,2-a]indole-9-carbonitrile (intermediate 17) (152 mg, 0.5 mmol) and commercially available thiomorpholine 1,1-dioxide (135 mg, 1.0 mmol).

EXAMPLE 44

11-Methyl-7-morpholin-4-yl-1-oxo-2,3,4,5-tetrahydro-[1,4]diazepino[1,2-a]indole-9-carbonitrile

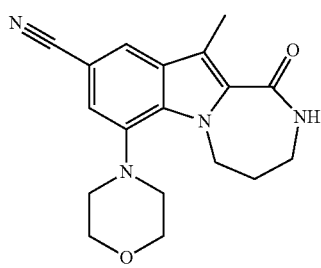 [SMILES: Cc1c2n(c3c(N4CCOCC4)cc(C#N)cc13)CCCNC2=O]

The title compound, off-white solid (16 mg, 10%), MS (ISP) m/z=325.5 [(M+H)⁺], mp 227° C., was prepared in accordance with the general method of example 6 from 7-bromo-11-methyl-1-oxo-2,3,4,5-tetrahydro-[1,4]diazepino[1,2-a]indole-9-carbonitrile (intermediate 14) (159 mg, 0.5 mmol) and commercially available morpholine (87.1 mg, 87.1 μl, 1.0 mmol).

EXAMPLE 45

7-Morpholin-4-yl-1-oxo-2,3,4,5-tetrahydro-[1,4]diazepino[1,2-a]indole-9-carbonitrile

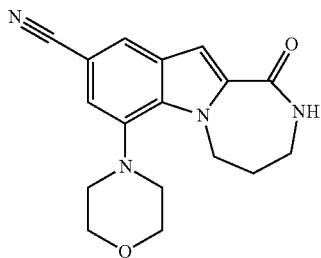 [SMILES: N#Cc1cc(N2CCOCC2)c2c(c1)cc1n2CCCNC1=O]

The title compound, light yellow solid (34 mg, 22%), MS (ISP) m/z=311.1 [(M+H)⁺], mp 221° C., was prepared in accordance with the general method of example 6 from 7-bromo-1-oxo-2,3,4,5-tetrahydro-[1,4]diazepino[1,2-a]indole-9-carbonitrile (intermediate 17) (152 mg, 0.5 mmol) and commercially available morpholine (87.1 mg, 87.1 μl, 1.0 mmol).

EXAMPLE 46

6-Morpholin-4-yl-1-oxo-3,4-dihydro-2H-pyrazino[1,2-a]indole-8-carbonitrile

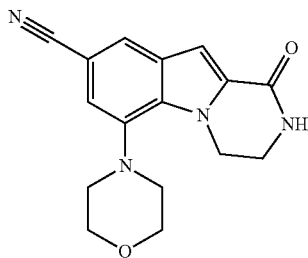 [SMILES: N#Cc1cc(N2CCOCC2)c2c(c1)cc1n2CCNC1=O]

The title compound, light grey solid (28 mg, 32%), MS (ISP) m/z=297.1 [(M+H)⁺], mp 280° C., was prepared in accordance with the general method of example 6 from 6-bromo-1-oxo-1,2,3,4-tetrahydro-pyrazino[1,2-a]indole-8-carbonitrile (intermediate 12) (85 mg, 0.29 mmol) and commercially available morpholine (51.1 mg, 51.1 μl, 0.58 mmol).

The invention claimed is:
1. A compound of formula I

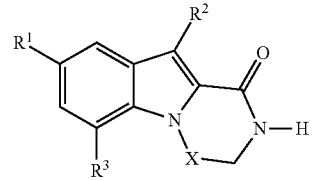

wherein
$R^1$ is halogen, lower alkyl, lower alkoxy, lower alkyl substituted by halogen, lower alkoxy substituted by halogen or cyano;
$R^2$ is hydrogen, $CF_3$ or lower alkyl;
$R^3$ is lower alkyl, lower alkenyl, lower alkynyl, heterocycloalkyl, lower alkyl substituted by cyano, cyano, benzyl substituted by halogen, 2-oxa-6-aza-spiro[3.3]hept-6-yl or is lower alkoxy substituted by halogen;
X is —CH$_2$— or —CH$_2$—CH$_2$—;
or a pharmaceutically acceptable acid addition salt, an enantiomer, diastereomer or a mixture of enantiomers or diastereomers.

2. The compound of claim 1 which compound has formula IA

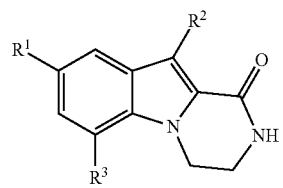

wherein
$R^1$ is halogen, lower alkyl, lower alkoxy, lower alkyl substituted by halogen, lower alkoxy substituted by halogen or cyano;
$R^2$ is hydrogen, $CF_3$ or lower alkyl;
$R^3$ is lower alkyl, lower alkenyl, lower alkynyl, heterocycloalkyl, lower alkyl substituted by cyano, cyano, benzyl substituted by halogen, 2-oxa-6-aza-spiro[3.3]hept-6-yl or is lower alkoxy substituted by halogen;
or a pharmaceutically acceptable acid addition salt an enantiomer, diastereomer or a mixture of enantiomers or diastereomers thereof.

3. The compound of claim 2, wherein the compound is:
8-Fluoro-6-methyl-3,4-dihydro-2H-pyrazino[1,2-a]indol-1-one,
8-Fluoro-6-isobutyl-10-methyl-3,4-dihydro-2H-pyrazino[1,2-a]indol-1-one,
8-Fluoro-6,10-dimethyl-3,4-dihydro-2H-pyrazino[1,2-a]indol-1-one,
8-Fluoro-10-methyl-6-morpholin-4-yl-3,4-dihydro-2H-pyrazino[1,2-a]indol-1-one,
8-Chloro-6,10-dimethyl-3,4-dihydro-2H-pyrazino[1,2-a]indol-1-one,
6-Ethyl-8-fluoro-10-methyl-3,4-dihydro-2H-pyrazino[1,2-a]indol-1-one,
6-(1,1-Dioxo-1λ⁶-thiomorpholin-4-yl)-8-fluoro-10-methyl-3,4-dihydro-2H-pyrazino[1,2-a]indol-1-one,
8-Chloro-6-ethyl-10-methyl-3,4-dihydro-2H-pyrazino[1,2-a]indol-1-one, 6-Allyl-8-fluoro-10-methyl-3,4-dihydro-2H-pyrazino[1,2-a]indol-1-one,
8-Fluoro-10-methyl-6-(3-methyl-butyl)-3,4-dihydro-2H-pyrazino[1,2-a]indol-1-one,
4-(8-Fluoro-10-methyl-1-oxo-1,2,3,4-tetrahydro-pyrazino[1,2-a]indol-6-yl)-butyronitrile,
8-Chloro-6-isobutyl-10-methyl-3,4-dihydro-2H-pyrazino[1,2-a]indol-1-one,
8-Fluoro-6-(4-fluoro-benzyl)-10-methyl-3,4-dihydro-2H-pyrazino[1,2-a]indol-1-one,
8-Fluoro-10-methyl-6-(2-oxa-6-aza-spiro[3.3]hept-6-yl)-3,4-dihydro-2H-pyrazino[1,2-a]indol-1-one,
8-Chloro-6-(1,1-dioxo-1λ$^6$-thiomorpholin-4-yl)-10-methyl-3,4-dihydro-2H-pyrazino[1,2-a]indol-1-one,
8-Chloro-10-methyl-6-morpholin-4-yl-3,4-dihydro-2H-pyrazino[1,2-a]indol-1-one,
6-(1,1-Dioxo-1λ$^6$-thiomorpholin-4-yl)-10-methyl-1-oxo-1,2,3,4-tetrahydro-pyrazino[1,2-a]indole-8-carbonitrile,
6-Ethynyl-8-fluoro-10-methyl-3,4-dihydro-2H-pyrazino[1,2-a]indol-1-one,
6-Isobutyl-1-oxo-1,2,3,4-tetrahydro-pyrazino[1,2-a]indole-8-carbonitrile,
8-Fluoro-6-(2-methylpropyl)-3,4-dihydro-2H-pyrazino[1,2-a]indol-1-one,
8-Fluoro-10-methyl-6-(2,2,2-trifluoroethoxy)-3,4-dihydro-2H-pyrazino[1,2-a]indol-1-one,
8-Chloro-6-(2-methylpropyl)-3,4-dihydro-2H-pyrazino[1,2-a]indol-1-one,
8-Chloro-6-methyl-3,4-dihydro-2H-pyrazino[1,2-a]indol-1-one,
8-Fluoro-10-methyl-1-oxo-3,4-dihydro-2H-pyrazino[1,2-a]indole-6-carbonitrile,
10-Methyl-1-oxo-6-(trifluoromethoxy)-3,4-dihydro-2H-pyrazino[1,2-a]indole-8-carbonitrile,
8-Methyl-6-(2-methylpropyl)-3,4-dihydro-2H-pyrazino[1,2-a]indol-1-one,
6,8-Dimethyl-3,4-dihydro-2H-pyrazino[1,2-a]indol-1-one,
8-Methoxy-6-(2-methylpropyl)-3,4-dihydro-2H-pyrazino[1,2-a]indol-1-one,
6-(2-Methylpropyl)-8-(trifluoromethoxy)-3,4-dihydro-2H-pyrazino[1,2-a]indol-1-one,
10-Methyl-6-morpholin-4-yl-1-oxo-3,4-dihydro-2H-pyrazino[1,2-a]indole-8-carbonitrile,
6-Morpholin-4-yl-1-oxo-3,4-dihydro-2H-pyrazino[1,2-a]indole-8-carbonitrile, or a pharmaceutically acceptable salt, an enantiomer, diastereomer or a mixture of enantiomers or diastereomers thereof.

4. The compound of claim 1 which compound has formula IB,

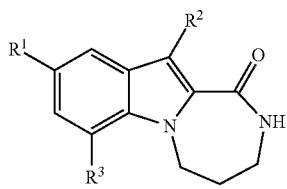

wherein
R$^1$ is halogen, lower alkyl, lower alkoxy, lower alkyl substituted by halogen, lower alkoxy substituted by halogen or cyano;
R$^2$ is hydrogen, CF$_3$ or lower alkyl;
R$^3$ is lower alkyl, lower alkenyl, lower alkynyl, heterocycloalkyl, lower alkyl substituted by cyano, cyano, benzyl substituted by halogen, 2-oxa-6-aza-spiro[3.3]hept-6-yl or is lower alkoxy substituted by halogen;
or a pharmaceutically acceptable acid addition salt, an enantiomer, diastereomer or a mixture of enantiomers or diastereomers.

5. The compound of claim 4, wherein the compound is
9-Fluoro-7-methyl-2,3,4,5-tetrahydro-[1,4]diazepino[1,2-a]indol-1-one,
9-Fluoro-7-isobutyl-2,3,4,5-tetrahydro-[1,4]diazepino[1,2-a]indol-1-one,
9-Chloro-7-(2-methylpropyl)-2,3,4,5-tetrahydro-[1,4]diazepino[1,2-a]indol-1-one,
9-Chloro-7-methyl-2,3,4,5-tetrahydro-[1,4]diazepino[1,2-a]indol-1-one,
9-Methyl-7-(2-methylpropyl)-2,3,4,5-tetrahydro-[1,4]diazepino[1,2-a]indol-1-one,
11-Methyl-7-(2-methylpropyl)-1-oxo-2,3,4,5-tetrahydro-[1,4]diazepino[1,2-a]indole-9-carbonitrile,
7,11-Dimethyl-1-oxo-2,3,4,5-tetrahydro-[1,4]diazepino[1,2-a]indole-9-carbonitrile,
9-Chloro-11-methyl-7-(2-methylpropyl)-2,3,4,5-tetrahydro-[1,4]diazepino[1,2-a]indol-1-one,
9-Chloro-7,11-dimethyl-2,3,4,5-tetrahydro-[1,4]diazepino[1,2-a]indol-1-one,
7-(2-Methylpropyl)-1-oxo-2,3,4,5-tetrahydro-[1,4]diazepino[1,2-a]indole-9-carbonitrile,
7-(1,1-Dioxo-1,4-thiazinan-4-yl)-11-methyl-1-oxo-2,3,4,5-tetrahydro-[1,4]diazepino[1,2-a]indole-9-carbonitrile,
7-(1,1-Dioxo-1,4-thiazinan-4-yl)-1-oxo-2,3,4,5-tetrahydro-[1,4]diazepino[1,2-a]indole-9-carbonitrile,
11-Methyl-7-morpholin-4-yl-1-oxo-2,3,4,5-tetrahydro-[1,4]diazepino[1,2-a]indole-9-carbonitrile, or
7-Morpholin-4-yl-1-oxo-2,3,4,5-tetrahydro-[1,4]diazepino[1,2-a]indole-9-carbonitrile, or
a pharmaceutically acceptable salt, an enantiomer, diastereomer or a mixture of enantiomers or diastereomers thereof.

6. A pharmaceutical composition comprising a compound according to claim 1 and a pharmaceutical acceptable carrier and/or adjuvant useful for stimulating neurogenesis in a patient in need thereof.

7. A process for the manufacture of a compound of formula I as defined in claim 1 which process comprises reacting a compound of formula

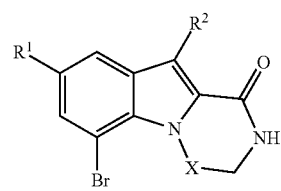

with a compound of formula

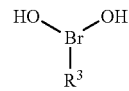

or in case of formation of a nitrogen carbon bond by Buchwald coupling reaction to a compound of formula
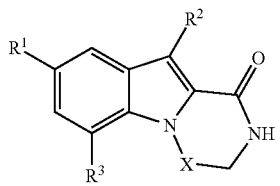
I
wherein the substituents are as described in claim 1, and, optionally, converting the compounds obtained into pharmaceutically acceptable acid addition salts.
8. A compound manufactured by a process according to claim 7.
\* \* \* \* \*